(12) United States Patent
Zhang et al.

(10) Patent No.: US 10,905,425 B2
(45) Date of Patent: Feb. 2, 2021

(54) ENDOSCOPIC REPOSABLE SURGICAL CLIP APPLIER

(71) Applicant: Covidien LP, Mansfield, MA (US)

(72) Inventors: Zhihua Zhang, ShenZhen (CN); Encheng Hu, Shanghai (CN)

(73) Assignee: COVIDIEN LP, Mansfield, MA (US)

( * ) Notice: Subject to any disclaimer, the term of this patent is extended or adjusted under 35 U.S.C. 154(b) by 338 days.

(21) Appl. No.: 15/768,854

(22) PCT Filed: Nov. 10, 2015

(86) PCT No.: PCT/CN2015/094172
§ 371 (c)(1),
(2) Date: Apr. 17, 2018

(87) PCT Pub. No.: WO2017/079890
PCT Pub. Date: May 18, 2017

(65) Prior Publication Data
US 2019/0053806 A1    Feb. 21, 2019

(51) Int. Cl.
*A61B 17/10* (2006.01)
*A61B 17/00* (2006.01)
*A61B 17/128* (2006.01)

(52) U.S. Cl.
CPC ...... *A61B 17/105* (2013.01); *A61B 17/00234* (2013.01); *A61B 17/1285* (2013.01); *A61B 2017/0023* (2013.01); *A61B 2017/00367* (2013.01); *A61B 2017/00469* (2013.01); *A61B 2017/00902* (2013.01)

(58) Field of Classification Search
CPC ........................................ A61B 17/128–1285
See application file for complete search history.

(56) References Cited

U.S. PATENT DOCUMENTS

| | | |
|---|---|---|
| 3,120,230 A | 2/1964 | Skold |
| 3,363,628 A | 1/1968 | Wood |
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,226,242 A | 10/1980 | Jarvik |
| 4,242,902 A | 1/1981 | Green |
| 4,296,751 A | 10/1981 | Blake, III et al. |

(Continued)

FOREIGN PATENT DOCUMENTS

| | | |
|---|---|---|
| AU | 2013254887 A1 | 11/2013 |
| CA | 1163889 A | 3/1984 |

(Continued)

OTHER PUBLICATIONS

Extended European Search Report corresponding to European Application No. EP 07 25 3905.9, completed Jan. 29, 2008; dated Feb. 7, 2008; (7 Pages).

(Continued)

*Primary Examiner* — Katrina M Stransky
*Assistant Examiner* — Brigid K Byrd

(57) ABSTRACT

A reposable surgical clip applier (10) is provided and includes a handle assembly (100), an endoscopic assembly (200) selectively connectable to a housing of the handle assembly (100), and a clip cartridge assembly (300) selectively loadable in and connectable to the endoscopic assembly (200).

21 Claims, 10 Drawing Sheets

(56) References Cited

U.S. PATENT DOCUMENTS

| | | | |
|---|---|---|---|
| 4,372,316 | A | 2/1983 | Blake, III et al. |
| 4,408,603 | A | 10/1983 | Blake, III et al. |
| 4,412,539 | A | 11/1983 | Jarvik |
| 4,418,694 | A | 12/1983 | Beroff et al. |
| 4,471,780 | A | 9/1984 | Menges et al. |
| 4,480,640 | A | 11/1984 | Becht |
| 4,480,641 | A | 11/1984 | Failla et al. |
| 4,487,204 | A | 12/1984 | Hrouda |
| 4,487,205 | A | 12/1984 | Di Giovanni et al. |
| 4,491,133 | A | 1/1985 | Menges et al. |
| 4,492,232 | A | 1/1985 | Green |
| 4,498,476 | A | 2/1985 | Cerwin et al. |
| 4,500,024 | A | 2/1985 | DiGiovanni et al. |
| 4,509,518 | A | 4/1985 | McGarry et al. |
| 4,512,345 | A | 4/1985 | Green |
| 4,522,207 | A | 6/1985 | Klieman et al. |
| 4,532,925 | A | 8/1985 | Blake, III |
| 4,534,351 | A | 8/1985 | Rothfuss et al. |
| 4,545,377 | A | 10/1985 | Cerwin et al. |
| 4,549,544 | A | 10/1985 | Favaron |
| 4,556,058 | A | 12/1985 | Green |
| 4,557,263 | A | 12/1985 | Green |
| 4,562,839 | A | 1/1986 | Blake, III et al. |
| 4,572,183 | A | 2/1986 | Juska |
| 4,576,165 | A | 3/1986 | Green et al. |
| 4,576,166 | A | 3/1986 | Montgomery et al. |
| 4,590,937 | A | 5/1986 | Deniega |
| 4,598,711 | A | 7/1986 | Deniega |
| 4,602,631 | A | 7/1986 | Funatsu |
| 4,611,595 | A | 9/1986 | Klieman et al. |
| 4,612,932 | A | 9/1986 | Caspar et al. |
| 4,616,650 | A | 10/1986 | Green et al. |
| 4,616,651 | A | 10/1986 | Golden |
| 4,624,254 | A | 11/1986 | McGarry et al. |
| 4,637,395 | A | 1/1987 | Caspar et al. |
| 4,646,740 | A | 3/1987 | Peters et al. |
| 4,647,504 | A | 3/1987 | Kimimura et al. |
| 4,658,822 | A | 4/1987 | Kees, Jr. |
| 4,660,558 | A | 4/1987 | Kees, Jr. |
| 4,662,373 | A | 5/1987 | Montgomery et al. |
| 4,662,374 | A | 5/1987 | Blake, III |
| 4,671,278 | A | 6/1987 | Chin |
| 4,671,282 | A | 6/1987 | Tretbar |
| 4,674,504 | A | 6/1987 | Klieman et al. |
| 4,681,107 | A | 7/1987 | Kees, Jr. |
| 4,696,396 | A | 9/1987 | Samuels |
| 4,702,247 | A | 10/1987 | Blake, III et al. |
| 4,706,668 | A | 11/1987 | Backer |
| 4,712,549 | A | 12/1987 | Peters et al. |
| 4,726,372 | A | 2/1988 | Perlin |
| 4,733,666 | A | 3/1988 | Mercer, Jr. |
| 4,759,364 | A | 7/1988 | Boebel |
| 4,765,335 | A | 8/1988 | Schmidt et al. |
| 4,777,949 | A | 10/1988 | Perlin |
| 4,796,625 | A | 1/1989 | Kees, Jr. |
| 4,799,481 | A | 1/1989 | Transue et al. |
| 4,815,466 | A | 3/1989 | Perlin |
| 4,821,721 | A | 4/1989 | Chin et al. |
| 4,822,348 | A | 4/1989 | Casey |
| 4,834,096 | A | 5/1989 | Oh et al. |
| 4,850,355 | A | 7/1989 | Brooks et al. |
| 4,854,317 | A | 8/1989 | Braun |
| 4,856,517 | A | 8/1989 | Collins et al. |
| 4,929,239 | A | 5/1990 | Braun |
| 4,931,058 | A | 6/1990 | Cooper |
| 4,934,364 | A | 6/1990 | Green |
| 4,957,500 | A | 9/1990 | Liang et al. |
| 4,966,603 | A | 10/1990 | Focelle et al. |
| 4,967,949 | A | 11/1990 | Sandhaus |
| 4,983,176 | A | 1/1991 | Cushman et al. |
| 4,988,355 | A | 1/1991 | Leveen et al. |
| 5,002,552 | A | 3/1991 | Casey |
| 5,026,379 | A | 6/1991 | Yoon |
| 5,030,224 | A | 7/1991 | Wright et al. |
| 5,030,226 | A | 7/1991 | Green et al. |
| 5,032,127 | A | 7/1991 | Frazee et al. |
| 5,035,692 | A | 7/1991 | Lyon et al. |
| 5,047,038 | A | 9/1991 | Peters et al. |
| 5,049,152 | A | 9/1991 | Simon et al. |
| 5,049,153 | A | 9/1991 | Nakao et al. |
| 5,053,045 | A | 10/1991 | Schmidt et al. |
| 5,059,202 | A | 10/1991 | Liang et al. |
| 5,062,563 | A | 11/1991 | Green et al. |
| 5,062,846 | A | 11/1991 | Oh et al. |
| 5,078,731 | A | 1/1992 | Hayhurst |
| 5,084,057 | A | 1/1992 | Green et al. |
| 5,100,416 | A | 3/1992 | Oh et al. |
| 5,100,420 | A | 3/1992 | Green et al. |
| 5,104,394 | A | 4/1992 | Knoepfler |
| 5,104,395 | A | 4/1992 | Thornton et al. |
| 5,112,343 | A | 5/1992 | Thornton |
| 5,122,150 | A | 6/1992 | Puig |
| 5,127,915 | A | 7/1992 | Mattson |
| 5,129,885 | A | 7/1992 | Green et al. |
| 5,156,608 | A | 10/1992 | Troidl et al. |
| 5,160,339 | A | 11/1992 | Chen et al. |
| 5,163,945 | A | 11/1992 | Ortiz et al. |
| 5,171,247 | A | 12/1992 | Hughett et al. |
| 5,171,249 | A | 12/1992 | Stefanchik et al. |
| 5,171,250 | A | 12/1992 | Yoon |
| 5,171,251 | A | 12/1992 | Bregen et al. |
| 5,171,252 | A | 12/1992 | Friedland |
| 5,171,253 | A | 12/1992 | Klieman |
| 5,192,288 | A | 3/1993 | Thompson et al. |
| 5,197,970 | A | 3/1993 | Green et al. |
| 5,199,566 | A | 4/1993 | Ortiz et al. |
| 5,201,746 | A | 4/1993 | Shichman |
| 5,201,900 | A | 4/1993 | Nardella |
| 5,207,691 | A | 5/1993 | Nardella |
| 5,207,692 | A | 5/1993 | Kraus et al. |
| 5,217,473 | A | 6/1993 | Yoon |
| 5,219,353 | A | 6/1993 | Garvey, III et al. |
| 5,246,450 | A | 9/1993 | Thornton et al. |
| 5,269,792 | A | 12/1993 | Kovac et al. |
| 5,281,228 | A | 1/1994 | Wolfson |
| 5,282,807 | A | 2/1994 | Knoepfler |
| 5,282,808 | A | 2/1994 | Kovac et al. |
| 5,282,832 | A | 2/1994 | Toso et al. |
| 5,289,963 | A | 3/1994 | McGarry et al. |
| 5,290,299 | A | 3/1994 | Fain et al. |
| 5,300,081 | A | 4/1994 | Young et al. |
| 5,304,183 | A | 4/1994 | Gourlay et al. |
| 5,306,280 | A | 4/1994 | Bregen et al. |
| 5,306,283 | A | 4/1994 | Conners |
| 5,312,426 | A | 5/1994 | Segawa et al. |
| 5,330,442 | A | 7/1994 | Green et al. |
| 5,330,487 | A | 7/1994 | Thornton et al. |
| 5,340,360 | A | 8/1994 | Stefanchik |
| 5,342,373 | A | 8/1994 | Stefanchik et al. |
| 5,354,304 | A | 10/1994 | Allen et al. |
| 5,354,306 | A | 10/1994 | Garvey, III et al. |
| 5,356,064 | A | 10/1994 | Green et al. |
| 5,359,993 | A | 11/1994 | Slater et al. |
| 5,366,458 | A | 11/1994 | Korthoff et al. |
| 5,366,459 | A | 11/1994 | Yoon |
| 5,368,600 | A | 11/1994 | Failla et al. |
| 5,381,943 | A | 1/1995 | Allen et al. |
| 5,382,253 | A | 1/1995 | Hogendijk |
| 5,382,254 | A | 1/1995 | McGarry et al. |
| 5,382,255 | A | 1/1995 | Castro et al. |
| 5,383,880 | A | 1/1995 | Hooven |
| 5,383,881 | A | 1/1995 | Green et al. |
| 5,395,375 | A | 3/1995 | Turkel et al. |
| 5,395,381 | A | 3/1995 | Green et al. |
| 5,403,327 | A | 4/1995 | Thornton et al. |
| 5,409,498 | A | 4/1995 | Braddock et al. |
| 5,413,584 | A | 5/1995 | Schulze |
| 5,423,835 | A | 6/1995 | Green et al. |
| 5,425,740 | A | 6/1995 | Hutchinson, Jr. |
| 5,431,667 | A | 7/1995 | Thompson et al. |
| 5,431,668 | A | 7/1995 | Burbank, III et al. |
| 5,431,669 | A | 7/1995 | Thompson et al. |
| 5,439,468 | A | 8/1995 | Schulze et al. |
| 5,441,509 | A | 8/1995 | Vidal et al. |

(56) References Cited

U.S. PATENT DOCUMENTS

| | | |
|---|---|---|
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A * | 6/1998 | Cuny .................. A61B 17/1285 227/901 |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |

(56) References Cited

U.S. PATENT DOCUMENTS

| | | |
|---|---|---|
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |

(56) References Cited

U.S. PATENT DOCUMENTS

| | | |
|---|---|---|
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,048,088 B2 | 11/2011 | Green et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,138 B2 | 3/2013 | Weisshaupt et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,828,023 B2 | 9/2014 | Neff et al. |
| 8,839,954 B2 | 9/2014 | Disch |

(56) References Cited

U.S. PATENT DOCUMENTS

| | | |
|---|---|---|
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,972 B1 | 3/2016 | Patel et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,810 B2 | 9/2016 | Cappola |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,526,565 B2 | 12/2016 | Strobl |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,136,939 B2 | 11/2018 | Minnelli et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2002/0123742 A1 | 9/2002 | Baxter et al. |
| 2003/0014060 A1 | 1/2003 | Wilson, Jr. et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0097970 A1 | 5/2004 | Hughett |
| 2004/0097971 A1 | 5/2004 | Hughett |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0079115 A1 | 4/2006 | Aranyi |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0124485 A1 | 6/2006 | Kennedy |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |

(56) References Cited

U.S. PATENT DOCUMENTS

| | | |
|---|---|---|
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0204115 A1 | 8/2009 | Dees, Jr. et al. |
| 2009/0209946 A1 | 8/2009 | Swayze et al. |
| 2009/0228023 A1 | 9/2009 | Cui |
| 2009/0261142 A1 | 10/2009 | Milliman et al. |
| 2009/0264904 A1 | 10/2009 | Aldrich et al. |
| 2009/0312775 A1 | 12/2009 | Gilkey et al. |
| 2009/0326558 A1 | 12/2009 | Cui et al. |
| 2010/0089970 A1 | 4/2010 | Smith et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0054498 A1 | 3/2011 | Monassevitch et al. |
| 2011/0087220 A1 | 4/2011 | Felder et al. |
| 2011/0087268 A1 | 4/2011 | Livneh |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0022526 A1 | 1/2012 | Aldridge et al. |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0041379 A1 | 2/2013 | Bodor et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2013/0325057 A1 | 12/2013 | Larson et al. |
| 2014/0074143 A1 | 3/2014 | Fitzgerald et al. |
| 2014/0188159 A1 | 7/2014 | Steege |
| 2014/0263565 A1 | 9/2014 | Lytle, IV et al. |
| 2014/0276970 A1 | 9/2014 | Messerly et al. |
| 2014/0371728 A1 | 12/2014 | Vaughn |
| 2015/0032131 A1 | 1/2015 | Sorrentino et al. |
| 2015/0196298 A1* | 7/2015 | Menn .................. A61B 17/105 606/143 |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2016/0004956 A1 | 1/2016 | Reynolds et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1 | 9/2016 | Gokharu |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |

(56) References Cited

U.S. PATENT DOCUMENTS

| | | |
|---|---|---|
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | |
|---|---|---|
| CN | 101836875 A | 9/2010 |
| CN | 103190939 A | 7/2013 |
| CN | 103251441 A | 8/2013 |
| CN | 104605911 B | 2/2017 |
| DE | 202005001664 U1 | 5/2005 |
| DE | 202007003398 U1 | 6/2007 |
| DE | 202009006113 U1 | 7/2009 |
| EP | 0000756 A1 | 2/1979 |
| EP | 0406724 A1 | 1/1991 |
| EP | 0514139 A2 | 11/1992 |
| EP | 0514139 A3 | 3/1993 |
| EP | 0732078 A2 | 9/1996 |
| EP | 1769757 A1 | 4/2007 |
| EP | 1468653 B1 | 11/2007 |
| EP | 2263570 B1 | 2/2014 |
| EP | 3132756 A1 | 2/2017 |
| GB | 2073022 A | 10/1981 |
| JP | 2003033361 A | 2/2003 |
| JP | 2006154230 A | 6/2006 |
| JP | 2006277221 A | 10/2006 |
| JP | 2008017876 A | 1/2008 |
| JP | 2011186812 A | 9/2011 |
| JP | 2013166982 A | 8/2013 |
| WO | 9003763 A1 | 4/1990 |
| WO | 9624294 A1 | 8/1996 |
| WO | 0042922 A1 | 7/2000 |
| WO | 0166001 A2 | 9/2001 |
| WO | 0167965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017084000 A1 | 5/2017 |
| WO | 2017146138 A1 | 8/2017 |

OTHER PUBLICATIONS

International Search Report corresponding to International Application No. PCT-US08-58185, completed Sep. 4, 2008; dated Sep. 9, 2008; (2 Pages).
International Search Report corresponding to International Application No. PCT-US08-59859, completed Sep. 14, 2008; dated Sep. 18, 2008; (2 Pages).
Extended European Search Report corresponding to European Application No. EP 07 25 3807.7, completed Nov. 7, 2008; dated Nov. 26, 2008; (11 Pages).
Extended European Search Report corresponding to European Application No. EP 09 25 2049.3, completed Dec. 11, 2009; dated Jan. 12, 2010; (3 Pages).
Extended European Search Report corresponding to European Application No. EP 09 25 2050.1, completed Dec. 23, 2009; dated Jan. 21, 2010; (3 Pages).
Extended European Search Report corresponding to European Application No. EP 09 25 2051.9, completed Dec. 21, 2009; dated Jan. 28, 2010; (3 Pages).
Extended European Search Report corresponding to European Application No. EP 09 25 2052.7, completed Nov. 16, 2009; dated Nov. 24, 2009; (3 Pages).
Extended European Search Report corresponding to European Application No. EP 09 25 2053.5, completed Nov. 24, 2009; dated Dec. 1, 2009; (3 Pages).
Extended European Search Report corresponding to European Application No. EP 09 25 2054.3, completed Jan. 7, 2010; dated Jan. 22, 2010; (3 Pages).
Extended European Search Report corresponding to European Application No. EP 09 25 2056.8, completed Jan. 8, 2010; dated Feb. 5, 2010; (3 Pages).
Extended European Search Report corresponding to European Application No. EP 10 25 0497.4, completed May 4, 2010; dated May 12, 2010; (6 Pages).
Extended European Search Report corresponding to European Application No. EP 10 25 2079.8, completed Mar. 8, 2011; dated Mar. 17, 2011; (3 Pages).
European Search Report corresponding to European Application No. EP 05 81 0218.7, completed Apr. 18, 2011; dated May 20, 2011; (3 pages).
European Search Report corresponding to European Application No. EP 05 80 7612.6, completed May 2, 2011; dated May 20, 2011; (3 pages).
Extended European Search Report corresponding to European Application No. EP 10 25 1737.2, completed May 9, 2011; dated May 20, 2011; (4 pages).
Extended European Search Report corresponding to European Application No. EP 11 25 0214.1, completed May 25, 2011; dated Jun. 1, 2011; (3 Pages).
Extended European Search Report corresponding to European Application No. EP 11 00 2681.2, completed May 31, 2011; dated Jun. 10, 2011; (3 Pages).
European Search Report corresponding to European Application No. EP 05 80 2686.5, completed Jan. 9, 2012; dated Jan. 18, 2012; (3 Pages).
Extended European Search Report corresponding to European Application No. EP 12 15 1313.9, completed Mar. 20, 2012 and dated Apr. 12, 2012; (5 Pages).
Extended European Search Report corresponding to European Application No. EP 12 16 1291.5, completed Apr. 24, 2012 and dated May 4, 2012; (5 Pages).
Extended European Search Report corresponding to European Application No. EP 12 16 5891.8, completed Jun. 12, 2012 and dated Jun. 20, 2012; (6 Pages).
Extended European Search Report corresponding to European Application No. EP 12 16 2288.0, completed Jun. 4, 2012 and dated Jul. 7, 2012; (6 Pages).
Extended European Search Report corresponding to European Application No. EP 12 16 4955.2, completed Aug. 23, 2012 and dated Sep. 4, 2012; (5 Pages).
Extended European Search Report corresponding to European Application No. EP 11 25 0754.6, completed Oct. 22, 2012 and dated Oct. 31, 2012; (6 Pages).
Extended European Search Report corresponding to European Application No. EP 12 18 6401.1, completed Nov. 22, 2012 and dated Nov. 30, 2012; (7 Pages).
Extended European Search Report corresponding to European Application No. EP 12 18 6448.2, completed Nov. 28, 2012 and dated Dec. 10, 2012; (6 Pages).
Extended European Search Report corresponding to European Application No. EP 12 19 1706.6, completed Dec. 19, 2012 and dated Jan. 8, 2013; (6 Pages).
Extended European Search Report corresponding to EP 12 19 8745.7, completed Mar. 19, 2013 and dated Apr. 11, 2013; (8 Pages).

(56) References Cited

OTHER PUBLICATIONS

Extended European Search Report corresponding to EP 12 15 2989.5, completed Apr. 9, 2013 and dated Apr. 18, 2013; (9 Pages).
Extended European Search Report corresponding to EP 08 73 2820.9, completed Jul. 2, 2013 and dated Jul. 9, 2013; (10 Pages).
Extended European Search Report corresponding to EP 13 17 2008.8, completed Aug. 14, 2013 and dated Aug. 28, 2013; (8 Pages).
Extended European Search Report corresponding to EP 13 16 6382.5, completed Nov. 19, 2013 and dated Nov. 28, 2013; (8 Pages).
Extended European Search Report corresponding to EP 11 25 0194.5, completed Nov. 25, 2013 and dated Dec. 3, 2013; (8 Pages).
Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
Extended European Search Report corresponding to EP 10 25 2112.7, completed Jul. 29, 2014 and dated Aug. 5, 2014; (8 pp).
Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
International Search Report for PCT/CN2015/094172 date of completion is Jul. 25, 2016 (8 pages).
Extended European Search Report dated Oct. 9, 2019 corresponding to counterpart Patent Application EP 15908020.9.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
International Search Report corresponding to Int'l Patent Appln. PCT/US2018/050316 dated Dec. 31, 2018.
International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2019.
Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.
Japanese Notice of Allowance dated Mar. 16, 2020 corresponding to counterpart Patent Application JP 2018-522796.
European Office Action corresponding to EP 12 152 989.5 dated May 4, 2015.
Australian Office Action corresponding to AU 2009212759 dated May 7, 2015.
Chinese Office Action corresponding to Int'l Appln No. CN 201210212642.9 dated Jun. 3, 2015.
European Office Action corresponding to Int'l Appln No. EP 04 719 757.9 dated Jun. 12, 2015.
European Office Action corresponding to Int'l Appln No. EP 13 166 382.5 dated Jun. 19, 2015.
Japanese Office Action corresponding to Int'l Application No. JP 2010-226908 dated Jun. 26, 2015.
Extended European Search Report corresponding to Int'l Application No. EP 15 15 5024.1 dated Jul. 17, 2015.
Extended European Search Report corresponding to Int'l Application No. EP 14 19 2026.4 dated Jul. 17, 2015.

(56) References Cited

OTHER PUBLICATIONS

Japanese Office Action corresponding to Int'l Application No. JP 2011-160126 dated Aug. 10, 2015.
Extended European Search Report corresponding to Int'l Application No. EP 14 15 0321.9 dated Sep. 23, 2015.
Extended European Search Report corresponding to Int'l Application No. EP 11 25 0675.3 dated Oct. 7, 2015.
Extended European Search Report corresponding to Int'l Application No. EP 11 25 0674.6 dated Oct. 7, 2015.
Extended European Search Report corresponding to Int'l Application No. EP 12 19 3447.5 dated Oct. 19, 2015.
Canadian Office Action corresponding to Int'l Application No. CA 2,675,875 dated Oct. 26, 2015.
Japanese Office Action corresponding to Int'l Application No. JP 2015-005629 dated Oct. 28, 2015.
Japanese Office Action corresponding to Int'l Application No. JP 2014-245081 dated Oct. 28, 2015.
Canadian Office Action corresponding to Int'l Application No. CA 2,675,921 dated Oct. 30, 2015.
Chinese Office Action corresponding to Int'l Application No. CN 201210555570.8 dated Nov. 2, 2015.
Canadian Office Action corresponding to Int'l Application No. CA 2,676,309 dated Nov. 3, 2015.
Canadian Office Action corresponding to Int'l Application No. CA 2,676,211 dated Nov. 24, 2015.
Canadian Office Action corresponding to Int'l Application No. CA 2,676,547 dated Nov. 25, 2015.
Extended European Search Report corresponding to Int'l Application No. EP 15 17 3809.3 dated Nov. 25, 2015.
Chinese Office Action corresponding to Int'l Application No. CN 201210586814.9 dated Dec. 2, 2015.
Extended European Search Report corresponding to Int'l Application No. EP 12 17 2940.4 dated Dec. 14, 2015.
Chinese First Office Action corresponding to Int'l Appln. No. CN 201210586826.1 dated Dec. 30, 2015.
Extended European Search Report corresponding to Int'l Appln. No. EP 15 18 5362.9 dated Feb. 12, 2016.
Extended European Search Report corresponding to Int'l Appln. No. EP 12 19 7813.4 dated Mar. 7, 2016.
Canadian Office Action corresponding to Int'l Appln. No. CA 2,676,465 dated Mar. 8, 2016.
Japanese Office Action corresponding to Int'l Appln. No. JP 2014-245081 dated Mar. 18, 2016.
Japanese Office Action corresponding to Int'l Appln. No. JP 2015-005629 dated Mar. 18, 2016.
Extended European Search Report corresponding to Int'l Appln. No. EP 15 19 3549.1 dated Mar. 22, 2016.
International Search Report and Written Opinion corresponding to Int'l Appln. No. PCT/CN2015/082199 dated Mar. 31, 2016.
Extended European Search Report corresponding to Int'l Appln. No. EP 15 19 7251.0 dated Apr. 8, 2016.
Extended European Search Report corresponding to Int'l Appln. No. EP 16 15 0739.7 dated May 17, 2016.
Canadian Office Action corresponding to Int'l Appln. No. CA 2,716,672 dated May 31, 2016.
Canadian Office Action corresponding to Int'l Appln. No. CA 2,717,448 dated May 31, 2016.
Canadian Office Action corresponding to Int'l Appln. No. CA 2,721,951 dated Jun. 1, 2016.
Partial European Search Report corresponding to Int'l Appln. No. EP 16 15 0287.7 dated Jun. 16, 2016.
Chinese Second Office Action corresponding to Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.

* cited by examiner

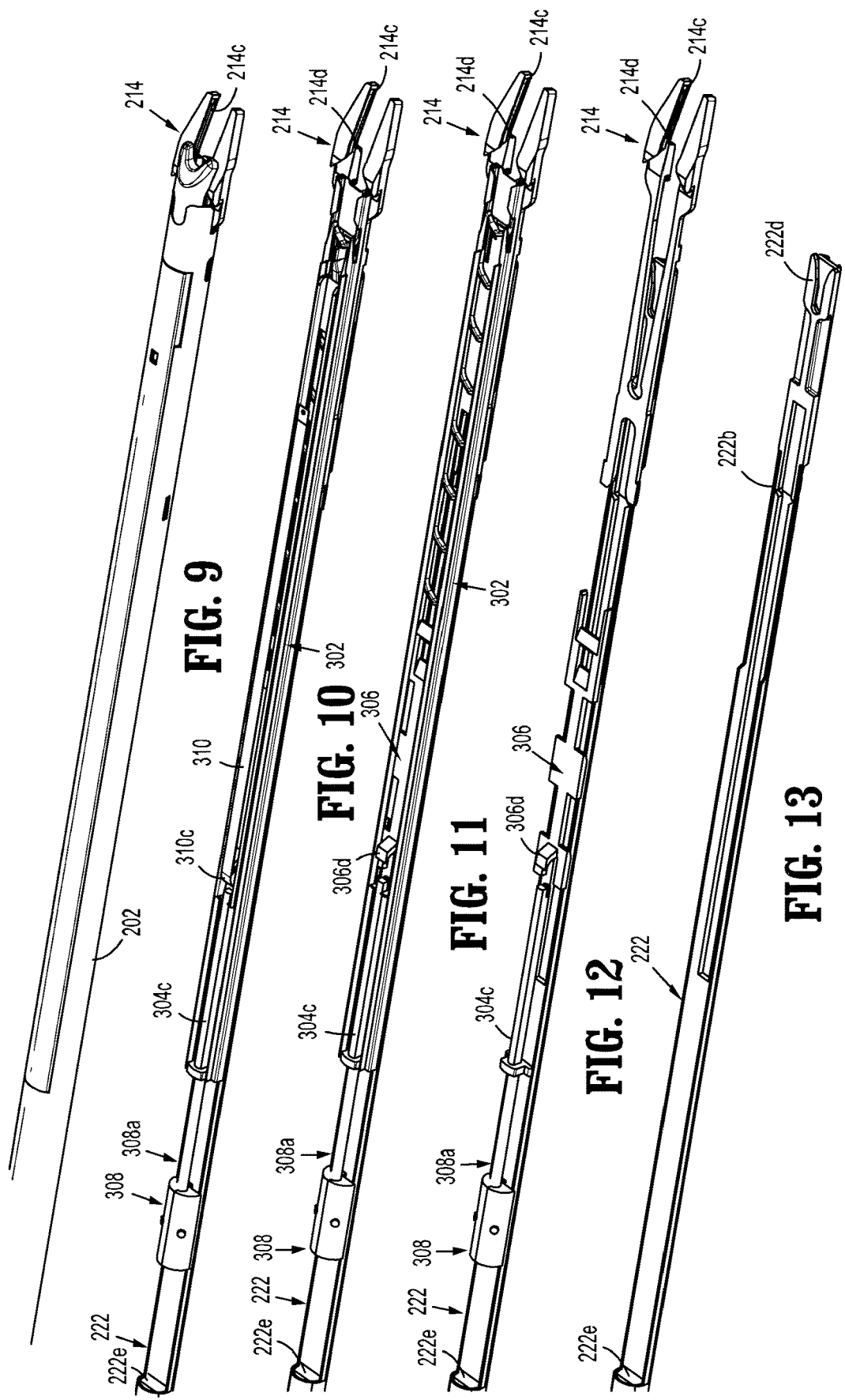

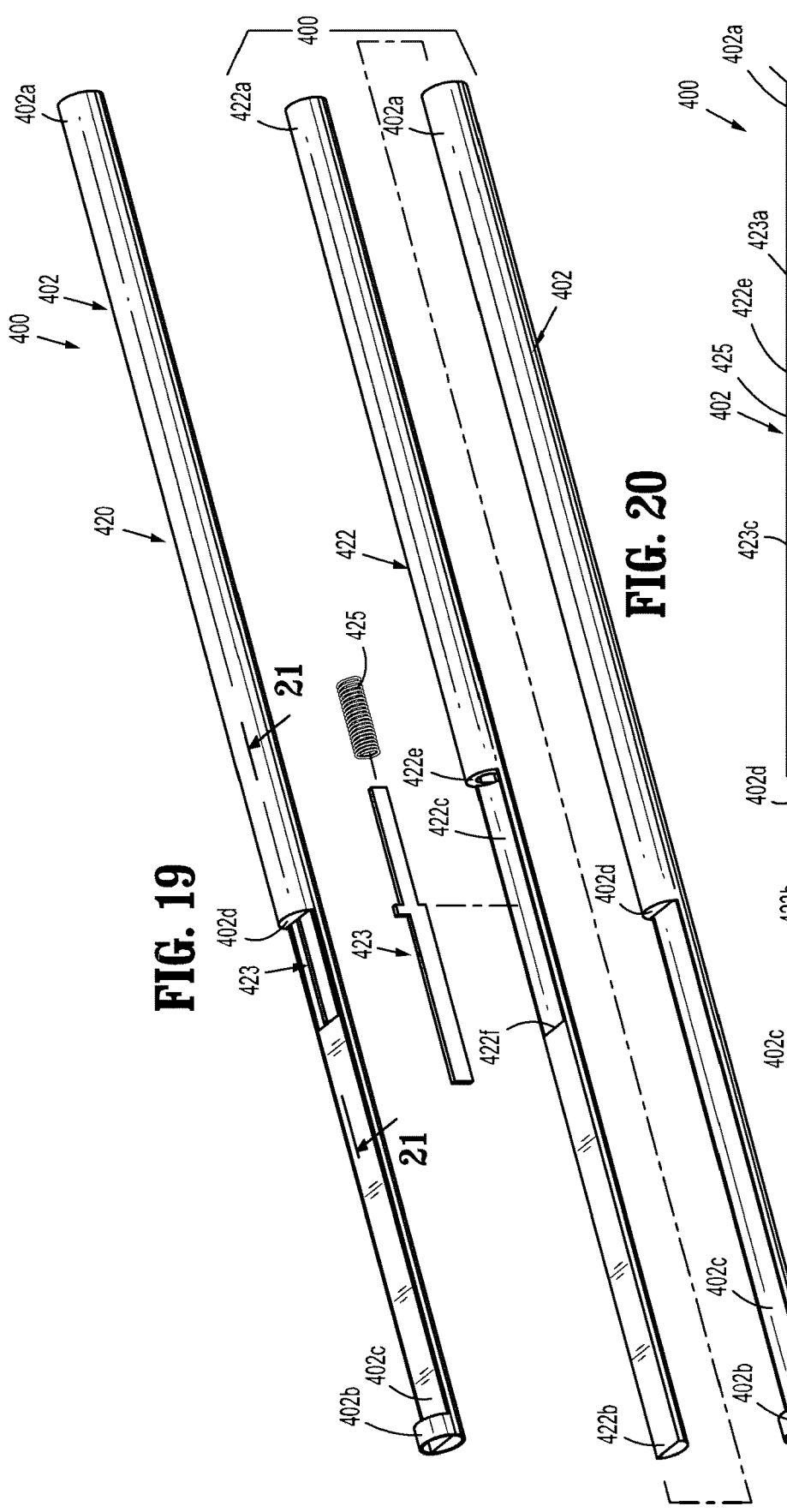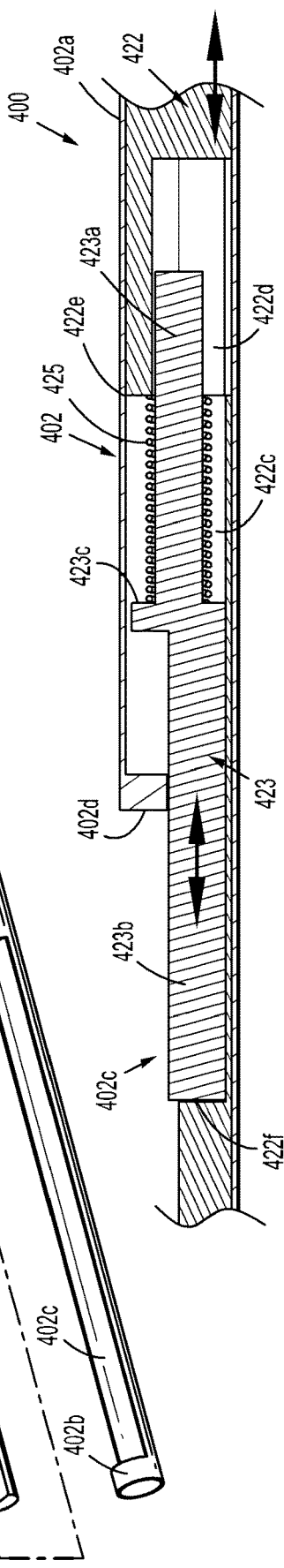

ENDOSCOPIC REPOSABLE SURGICAL CLIP APPLIER

CROSS-REFERENCE TO RELATED APPLICATIONS

This application is a National Stage Application of PCT/CN2015/094172 under 35USC § 371 (a), the disclosure of the above-identified application is hereby incorporated by reference in its entirety.

BACKGROUND

Technical Field

The present disclosure relates to surgical clip appliers. More particularly, the present disclosure relates to endoscopic reposable surgical clip appliers having a reusable handle assembly, a reusable shaft assembly, and a disposable clip cartridge assembly.

Description of Related Art

Endoscopic staplers and clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often apply a surgical clip to a blood vessel or another duct to prevent the flow of body fluids therethrough during the procedure. An endoscopic clip applier is known in the art for applying a single clip during an entry to the body cavity. Such clips are typically fabricated from a biocompatible material and are usually compressed over a vessel. Once applied to the vessel, the compressed clip terminates the flow of fluid therethrough.

Endoscopic clip appliers that are able to apply multiple clips in endoscopic or laparoscopic procedures during a single entry into the body cavity are described in commonly-assigned U.S. Pat. Nos. 5,084,057 and 5,100,420 to Green et al., which are both incorporated by reference in their entirety. Another multiple endoscopic clip applier is disclosed in commonly-assigned U.S. Pat. No. 5,607,436 by Pratt et al., the contents of which is also hereby incorporated by reference herein in its entirety. These devices are typically, though not necessarily, used during a single surgical procedure. U.S. Pat. No. 5,695,502 to Pier et al., the disclosure of which is hereby incorporated by reference herein, discloses a resterilizable surgical clip applier. The clip applier advances and forms multiple clips during a single insertion into the body cavity. This resterilizable clip applier is configured to receive and cooperate with an interchangeable clip magazine so as to advance and form multiple clips during a single entry so into a body cavity.

During endoscopic or laparoscopic procedures it may be desirable and/or necessary to use different size surgical clips depending on the underlying tissue or vessels to be ligated. In order to reduce overall costs of a surgical clip applier, it is desirable for a single surgical clip applier to be loadable with and capable of firing different size surgical clips as needed.

In addition, in order to reduce overall costs of a surgical clip applier, it is desirable to provide a surgical clip applier having components which may be reused (following proper cleaning, sterilizing and reconditioning procedures) multiple times, and which limits the number of disposable components thereof.

Accordingly, a need exists for improved endoscopic surgical clip appliers that include reusable handle assemblies, reusable shaft assemblies, and disposable clip cartridge assemblies.

SUMMARY

The present disclosure relates to reposable endoscopic surgical clip appliers.

According to an aspect of the present disclosure, a reposable surgical clip applier is provided and includes a handle assembly, an endoscopic assembly, and a clip cartridge assembly.

The handle assembly includes a housing defining a bore therein; a fixed handle extending from the housing; and a trigger pivotally connected to the fixed handle, the trigger including an actuating end disposed within the bore of the housing.

The endoscopic assembly is selectively connectable to the housing of the handle assembly. The endoscopic assembly includes an outer tube defining a lumen therethrough, the outer tube including a proximal end and a distal end; a pair of jaws fixedly supported and extending from the distal end of the outer tube; and a drive assembly slidably supported in the lumen of the outer tube.

The drive assembly includes a shaft pusher tube slidably supported in the lumen of the outer tube, the shaft pusher tube including a proximal end, a distal end and defining a lumen therethrough, wherein a radial flange is provided at the proximal end of the shaft pusher tube.

The drive assembly also includes a closure drive rod slidably disposed within the lumen of the shaft pusher tube, the closure drive rod having a proximal end projecting from the proximal end of the outer tube and engagable by the actuating end of the trigger, and a distal end selectively engagable with the pair of jaws to approximate the pair of jaws, wherein a shoulder is provided at the proximal end of the closure drive rod.

The drive assembly further includes a biasing member interposed between the shoulder of the closure drive rod and the radial flange of the shaft pusher tube.

The clip cartridge assembly is selectively connectable to the distal end of the outer tube, and to the distal end of the shaft pusher tube. The clip cartridge assembly includes a clip tray; a plurality of surgical clips slidably supported in the clip tray; a clip follower slidably disposed within the clip tray and disposed proximal of the plurality of surgical clips; a biasing member tending to urge the clip follower in a distal direction; and a clip pusher bar slidably supported adjacent the clip tray, wherein the clip pusher bar includes a proximal end configured for engagement by the distal end of the shaft pusher tube, and a distal end configured to engage a distal-most clip of the plurality of surgical clips.

In operation, during an initial actuation of the trigger, the actuating end of the trigger may act on the proximal end of the closure drive rod of the endoscopic assembly to distally advance the closure drive rod. The closure drive rod may act on the biasing member to distally advance the biasing member against the radial flange of the shaft pusher tube to distally advance the shaft pusher tube. The shaft pusher tube may act on the clip pusher bar to distally advance the clip pusher bar of the clip cartridge assembly and load a distal-most surgical clip thereof into the pair of jaws.

The endoscopic assembly may include a stop member supported in the outer tube thereof. The stop member may be disposed distal of the radial flange of the shaft pusher tube. The distal advancement of the shaft pusher tube may be stopped by the stop member.

In operation, following the stop member stopping the distal advancement of the shaft pusher tube, during a further actuation of the trigger, the actuating end of the trigger may act on the proximal end of the closure drive rod of the endoscopic assembly to further distally advance the closure drive rod. The closure drive rod may act on the biasing member to compress the biasing member between the radial flange of the shaft pusher tube and the shoulder of the closure drive rod.

In operation, during the further actuation of the trigger, the distal end of the closure drive rod may act on the pair of jaws to approximate the pair of jaws and to form any surgical clip loaded therein.

The clip pusher bar of the clip cartridge assembly may remain in a distal position during the approximation of the pair of jaws.

The handle assembly may include an end cap selectively securable to a proximal end of the housing.

According to another aspect of the present disclosure, an endoscopic assembly is configured for selective connection to a handle assembly and is actuatable by a trigger of the handle assembly. The endoscopic assembly includes an outer tube defining a lumen therethrough, the outer tube including a proximal end and a distal end; a pair of jaws fixedly supported and extending from the distal end of the outer tube, the pair of jaws being movable between an open position and a closed position, wherein the pair of jaws are configured to form a surgical clip loaded therewithin when the pair of jaws are actuated from the open position to the closed position; and a drive assembly slidably supported in the lumen of the outer tube.

The drive assembly includes a shaft pusher tube slidably supported in the lumen of the outer tube, the shaft pusher tube including a proximal end, a distal end and defining a lumen therethrough, wherein a radial flange is provided at the proximal end of the shaft pusher tube.

The drive assembly also includes a closure drive rod slidably disposed within the lumen of the shaft pusher tube, the closure drive rod having a proximal end projecting from the proximal end of the outer tube and engagable by the trigger of the handle assembly, and a distal end configured to selectively engage the pair of jaws to move the pair of jaws to the closed position, wherein a shoulder is provided at the proximal end of the closure drive rod.

The drive assembly further includes a biasing member interposed between the shoulder of the closure drive rod and the radial flange of the shaft pusher tube.

In operation, during an initial distal advancement of closure drive rod, the shoulder of the closure drive rod may act on the biasing member to distally advance the biasing member against the radial flange of the shaft pusher tube to distally advance the shaft pusher tube. The shaft pusher tube may act on a clip cartridge assembly load in the outer tube to advance a distal-most surgical clip of the clip cartridge assembly into the pair of jaws.

The endoscopic assembly may include a stop member supported in the outer tube thereof, wherein the stop member is disposed distal of the radial flange of the shaft pusher tube. The distal advancement of the shaft pusher tube may be stopped by the stop member.

In operation, following the stop member stopping the distal advancement of the shaft pusher tube, during a further advancement of the closure drive rod, the closure drive rod may act on the biasing member to compress the biasing member between the radial flange of the shaft pusher tube and the shoulder of the closure drive rod.

In operation, during the further advancement of the closure drive rod, the distal end of the closure drive rod may act on the pair of jaws to approximate the pair of jaws and to form any surgical clip loaded therein.

According to a further aspect of the present disclosure, a reposable surgical clip applier is provided comprising a handle assembly, an endoscopic assembly, and a clip cartridge assembly.

The handle assembly includes a housing; and a trigger pivotally connected to the housing, the trigger including an actuating end disposed within the housing.

The endoscopic assembly is selectively connectable to the housing of the handle assembly. The endoscopic assembly includes an outer tube defining a lumen therethrough and a window in a distal end thereof; a pair of jaws fixedly supported and extending from a distal end of the outer tube; and a drive assembly slidably supported in the lumen of the outer tube.

The drive assembly includes a shaft pusher tube slidably supported in the lumen of the outer tube, the shaft pusher tube including a proximal end, a distal end and defining a lumen therethrough, wherein a radial flange is provided at the proximal end of the shaft pusher tube.

The drive assembly also includes a closure drive rod slidably disposed within the lumen of the shaft pusher tube, the closure drive rod having a proximal end projecting from the proximal end of the outer tube and engagable by the actuating end of the trigger, and a distal end selectively engagable with the pair of jaws to approximate the pair of jaws, wherein a shoulder is provided at the proximal end of the closure drive rod.

The drive assembly further includes a biasing member interposed between the shoulder of the closure drive rod and the radial flange of the shaft pusher tube.

The clip cartridge assembly is selectively disposable within the window of the outer tube, and selectively connectable to the distal end of the shaft pusher tube. The clip cartridge assembly includes a clip tray; a plurality of surgical clips slidably supported in the clip tray; a clip follower slidably disposed within the clip tray and disposed proximal of the plurality of surgical clips; a biasing member tending to urge the clip follower in a distal direction; and a clip pusher bar slidably supported adjacent the clip tray, wherein the clip pusher bar includes a proximal end configured for engagement by the distal end of the shaft pusher tube, and a distal end configured to engage a distal-most clip of the plurality of surgical clips.

In operation, during an initial actuation of the trigger, the actuating end of the trigger may act on the proximal end of the closure drive rod of the endoscopic assembly to distally advance the closure drive rod. The closure drive rod may act on the biasing member to distally advance the biasing member against the radial flange of the shaft pusher tube to distally advance the shaft pusher tube. The shaft pusher tube may act on the clip pusher bar to distally advance the clip pusher bar of the clip cartridge assembly and load a distal-most surgical clip thereof into the pair of jaws.

The endoscopic assembly may include a stop member supported in the outer tube thereof, wherein the stop member is disposed distal of the radial flange of the shaft pusher tube. Distal advancement of the shaft pusher tube may be stopped by the stop member.

In operation, following the stop member stopping the distal advancement of the shaft pusher tube, during a further actuation of the trigger, the actuating end of the trigger may act on the proximal end of the closure drive rod of the endoscopic assembly to further distally advance the closure drive rod. The closure drive rod may act on the biasing member to compress the biasing member between the radial flange of the shaft pusher tube and the shoulder of the closure drive rod.

In operation, during the further actuation of the trigger, the distal end of the closure drive rod may act on the pair of jaws to approximate the pair of jaws and to form any surgical clip loaded therein.

The clip pusher bar of the clip cartridge assembly may remain in a distal position during the approximation of the pair of jaws.

BRIEF DESCRIPTION OF THE DRAWINGS

Particular embodiments of surgical clip appliers are disclosed herein with reference to the drawings wherein:

FIG. 9 is a perspective view of a distal end of an endoscopic shaft assembly with a cartridge assembly loaded therein, in accordance with the present disclosure, of the reposable endoscopic surgical clip applier of the present disclosure;

FIG. 10 is a perspective view of a distal end of the endoscopic shaft assembly with an outer tube removed therefrom, and with a cover of the cartridge assembly removed therefrom;

FIG. 11 is a perspective view of a distal end of the endoscopic shaft assembly with the outer tube removed therefrom, and with the cover, a constant force spring, and a stack of surgical clips of the cartridge assembly removed therefrom;

FIG. 12 is a perspective view of a distal end of the endoscopic shaft assembly with the outer tube removed therefrom, and with the cover, the constant force spring, the stack of surgical clips, and a clip tray of the cartridge assembly removed therefrom;

FIG. 13 is a perspective view of a distal end of a main closure drive rod of the endoscopic shaft assembly;

FIG. 19 is a schematic, perspective view of an endoscopic shaft assembly according to another embodiment of the present disclosure;

FIG. 20 is a perspective view, with parts separated, of the endoscopic shaft assembly of FIG. 19;

FIG. 21 is a cross-sectional view as taken through 21-21 of FIG. 19; and

DETAILED DESCRIPTION OF EMBODIMENTS

Figure 1:
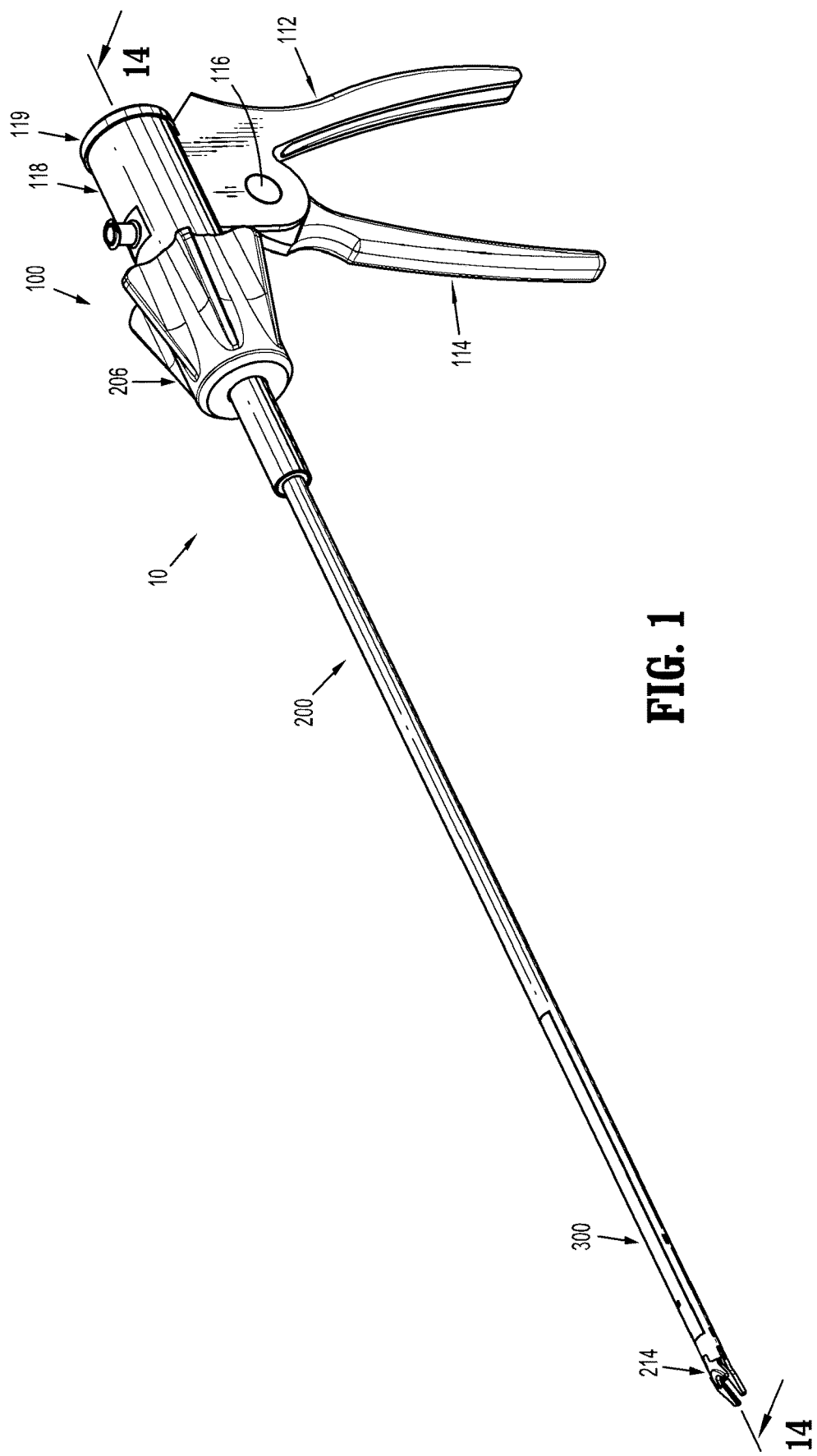
FIG. 1 is a top, front, perspective view, of a reposable endoscopic surgical clip applier, in accordance with the present disclosure.

Embodiments of reposable surgical clip appliers, in accordance with the present disclosure, will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Figure 2:
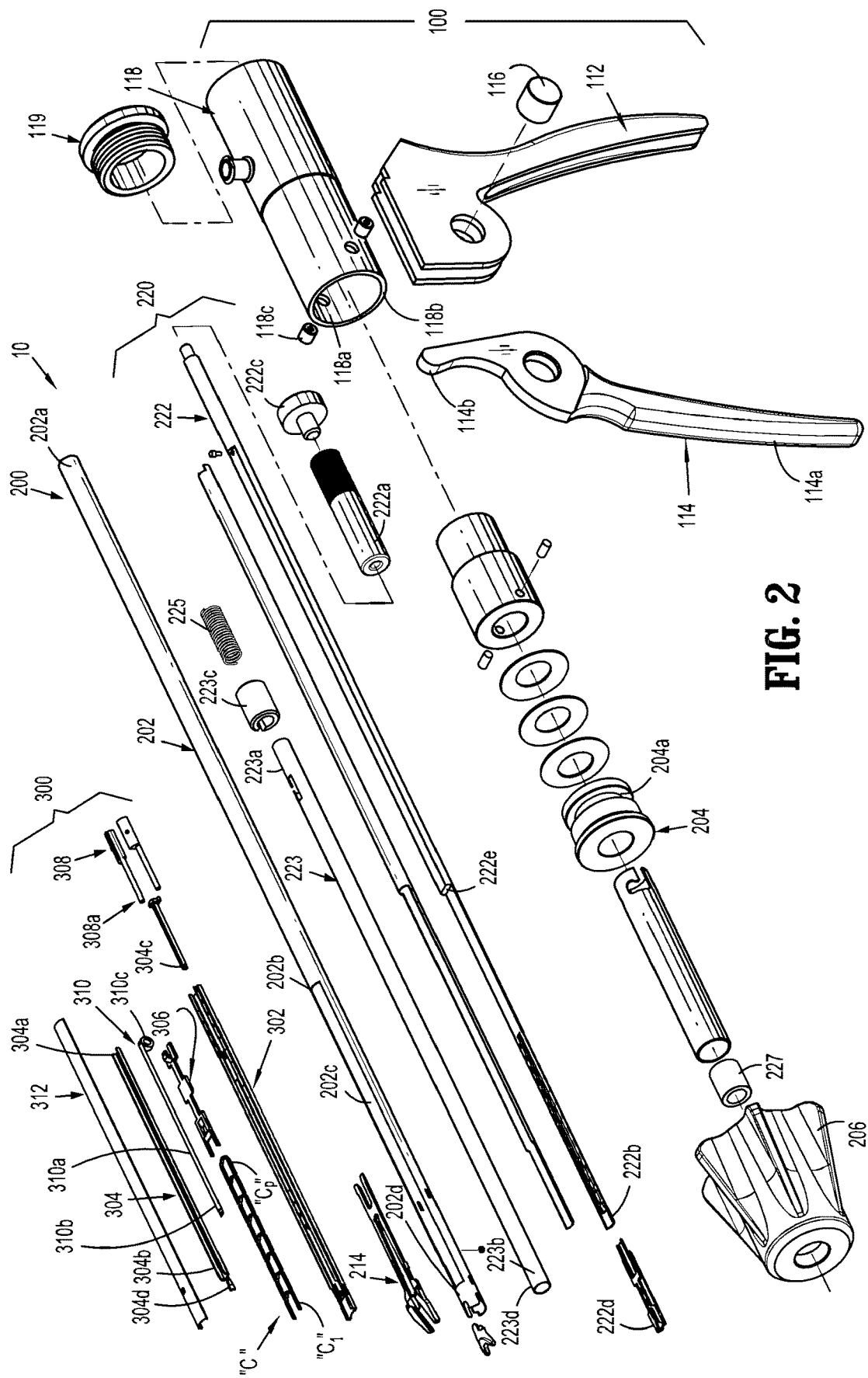
FIG. 2 is a perspective view, with parts separated, of the reposable endoscopic surgical clip applier of FIG. 1.
Figure 3:
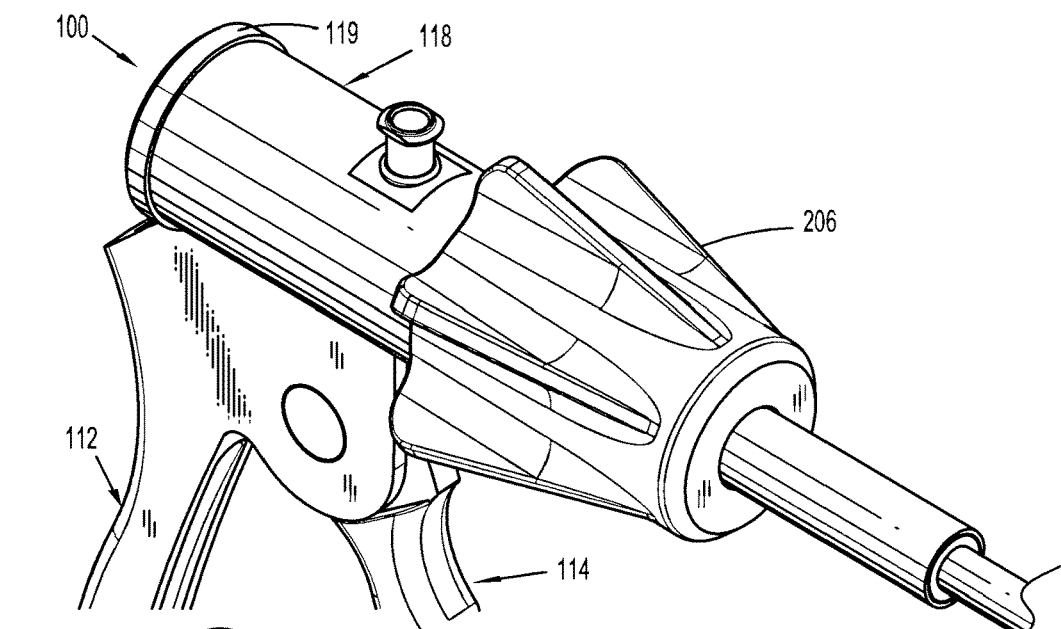
FIG. 3 is a distal, perspective view of a handle assembly of the reposable endoscopic surgical clip applier of FIGS. 1-2.
Figure 4:
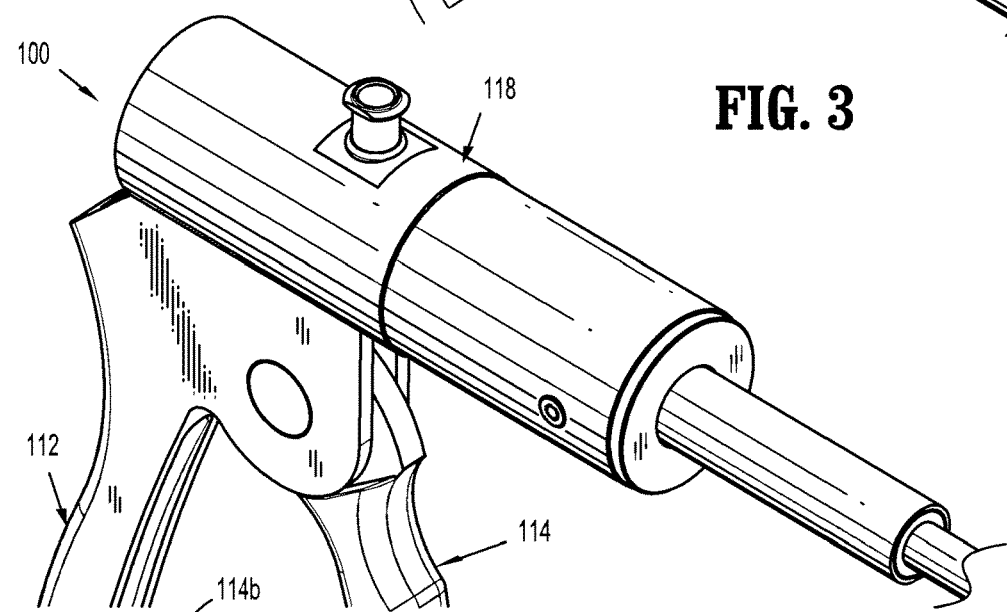
FIG. 4 is a distal, perspective view of the handle assembly of FIGS. 1-3, with a knob removed therefrom.
Figure 5:
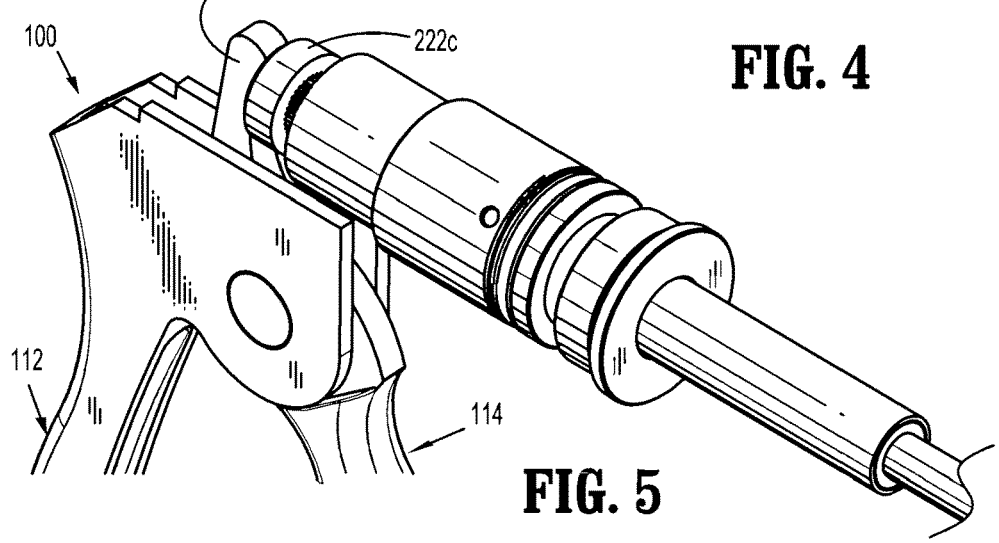
FIG. 5 is a distal, perspective view of the handle assembly of FIGS. 1-4, with the knob and a barrel removed therefrom.
Figure 6:
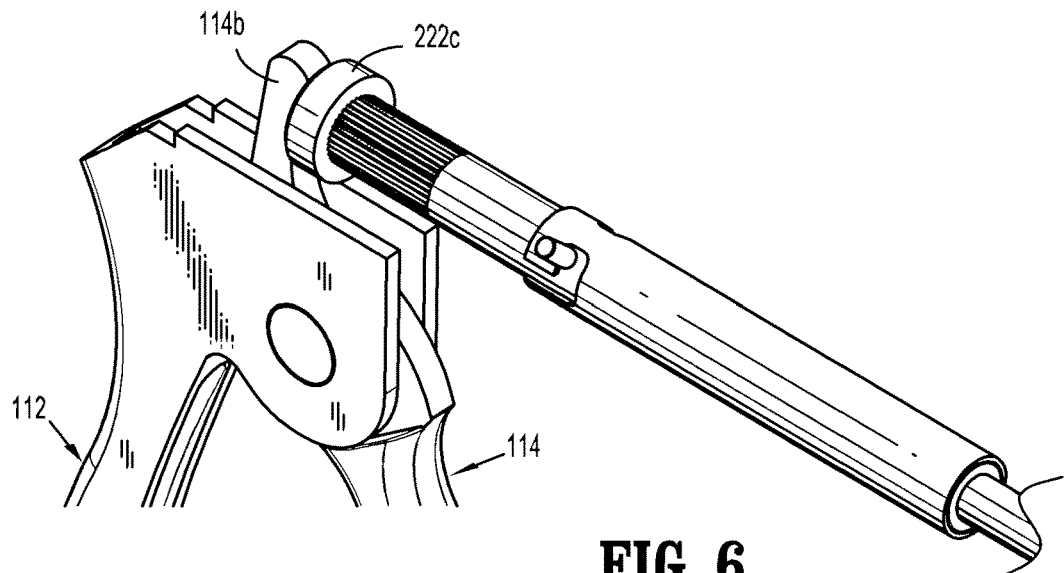
FIG. 6 is a distal, perspective view of the handle assembly of FIGS. 1-5, with the knob, the barrel, and a distal collar removed therefrom.
Figure 7:
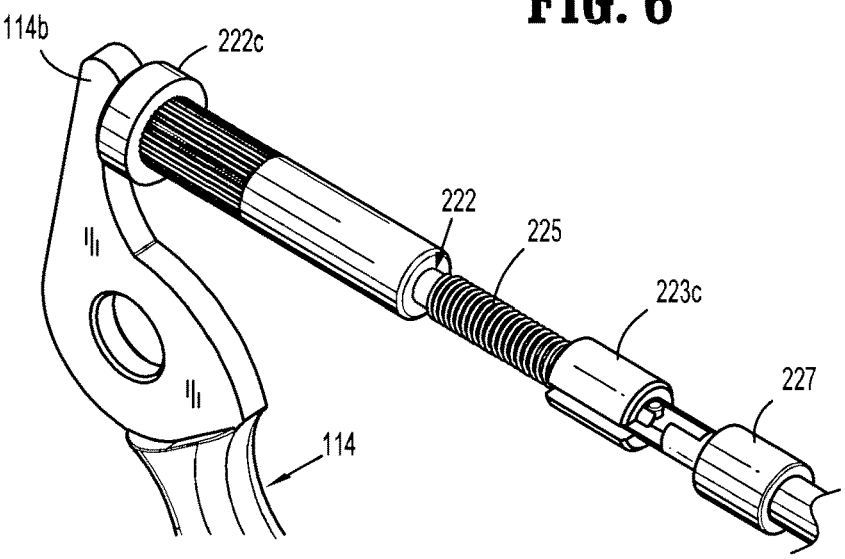
FIG. 7 is a distal, perspective view of the handle assembly of FIGS. 1-6, with the knob, the barrel, the distal collar, and a fixed handle removed therefrom.
Figure 8:
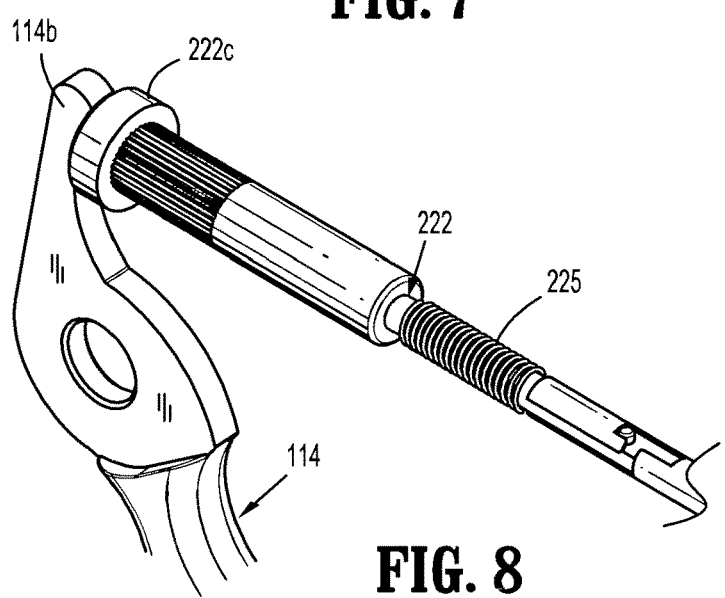
FIG. 8 is a distal, perspective view of the handle assembly of FIGS. 1-7, with the knob, the barrel, the distal collar, the fixed handle, and a cuff removed therefrom.
Figure 14:
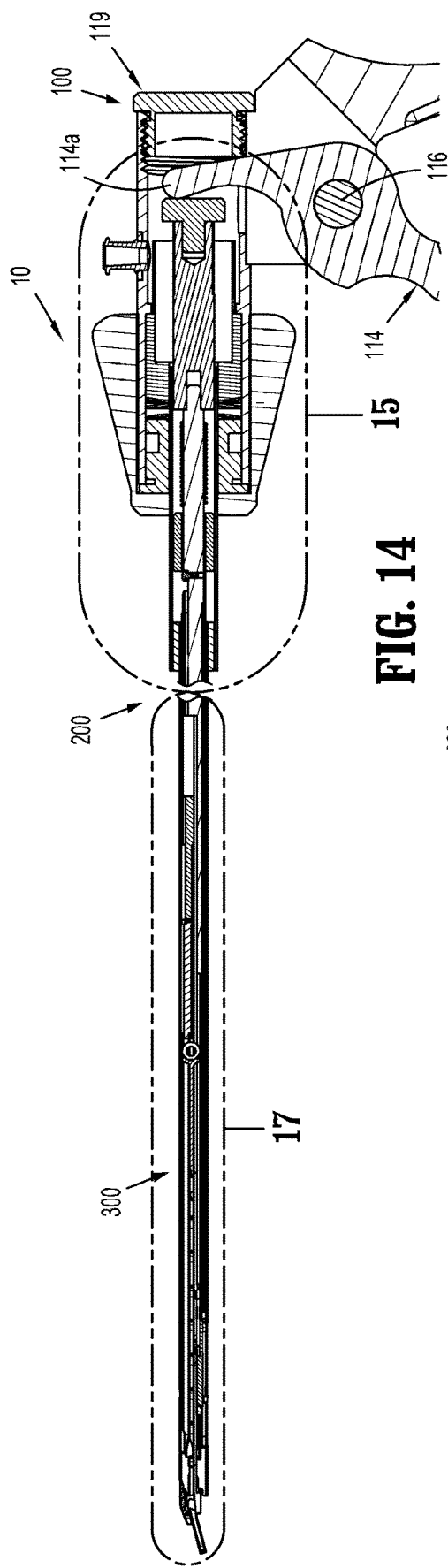
FIG. 14 is a cross-sectional view of the reposable endoscopic surgical clip applier, as taken through 14-14 of FIG. 1.
Figure 15:
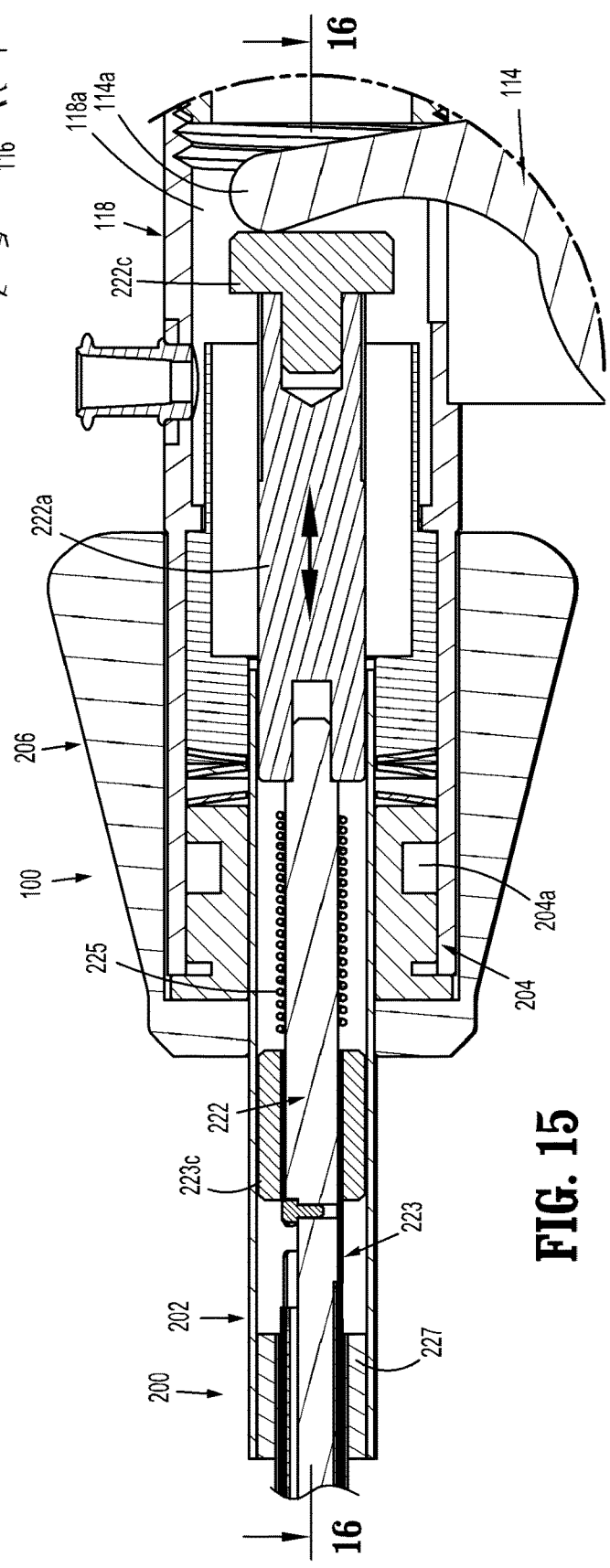
FIG. 15 is an enlarged view of the indicated area of detail of FIG. 14.
Figure 16:
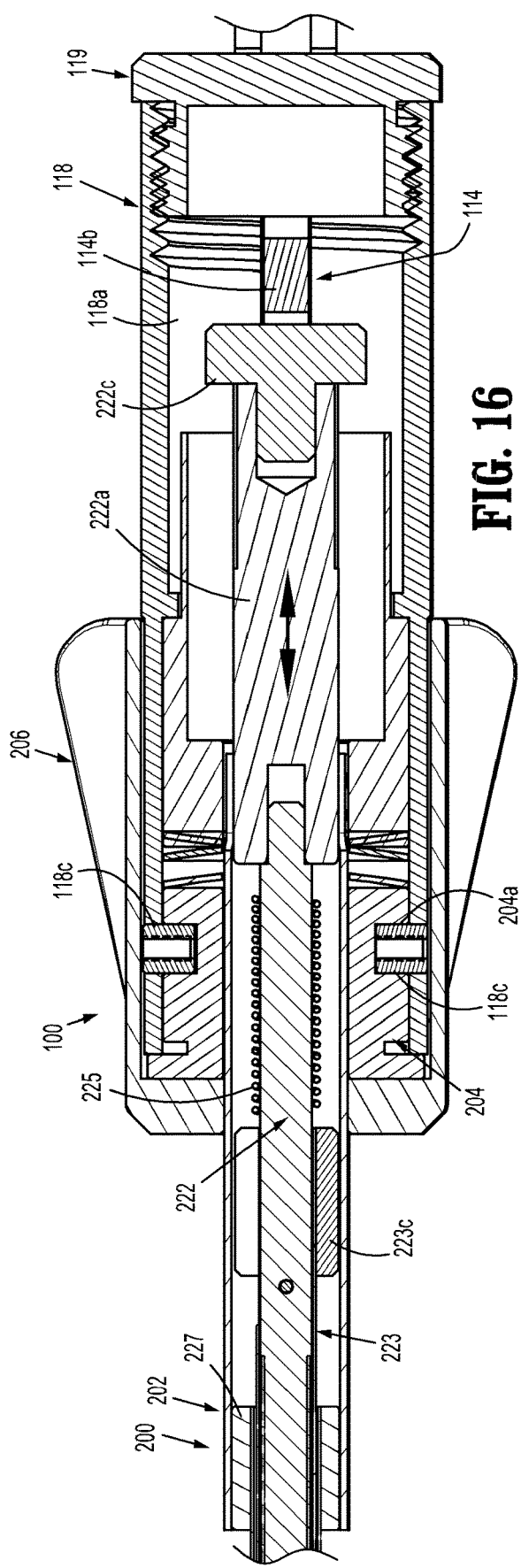
FIG. 16 is a cross-sectional view as taken through 16-16 of FIG. 15.
Figure 17:
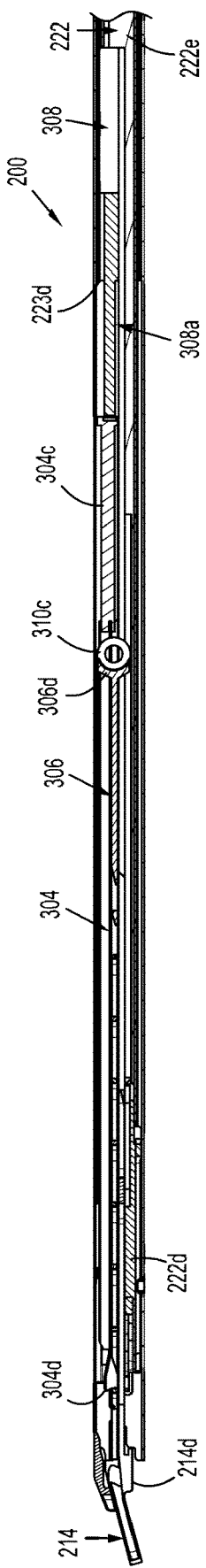
FIG. 17 is an enlarged view of the indicated area of detail of FIG. 14.

Referring initially to FIGS. 1-2, a surgical clip applier in accordance with an embodiment of the present disclosure is generally designated as 10. Surgical clip applier 10 includes a handle assembly 100, an elongated outer tube or endoscopic assembly 200 projecting from or extending from handle assembly 100, and a clip cartridge assembly 300 that can be removably and selectively mounted on/in a distal end of endoscopic assembly 200. As will be described in greater detail below, a plurality of surgical clips "C" (FIG. 2) is loaded into clip cartridge assembly 300. Also, as will be described in greater detail below, in operation, as handle assembly 100 is actuated, a single surgical clip "C" is fired and formed around a vessel to be ligated.

Handle assembly 100, as shown in FIGS. 1-8, includes a fixed handle 112 and a squeezable trigger 114 pivotally attached to fixed handle 112 at pivot shaft 116. Squeezable trigger 114 includes a proximal actuating end 114b, which extends proximally beyond pivot shaft 116, and which extends into a bore 118a of a barrel 118 supported on fixed handle 112.

A barrel 118 is supported on fixed handle 112 and is configured to receive a proximal end of endoscopic assembly 200. Barrel 118 defines a lumen or bore 118a therethrough. A threaded end cap 119 closes a proximal end of barrel 118. As seen in FIG. 2, a nose 118b of barrel 118 includes a pair of diametrically opposed nubs 118c projecting radially inward therefrom, and which are configured and dimensioned to slidably engage an annular outer channel or race 204a of a distal collar 204 of endoscopic assembly 200.

With reference to FIGS. 2-18C, endoscopic assembly 200 supports and/or includes a main drive assembly or advancing mechanism 220 removably supportable within bore 118b of barrel 118 or removably connectable to barrel 118. Main drive assembly 220 includes a main closure drive rod 222 having a proximal end 222a and a distal end 222b. Proximal end 222a of main closure drive rod 222 supports a flange, piston or drive head 222c thereon. Distal end 222b of main closure drive rod 222 defines a V-shaped cam groove 222d formed therein, which is configured and dimensioned to selectively engage cam wedges 214d of a pair of jaws 214 of endoscopic assembly 200, to thereby effectuate a closure or approximation of the pair of jaws 214.

Main closure drive rod 222 further defines a distally facing shoulder 222e along a length thereof. Shoulder 222e of main closure drive rod 222 is configured and dimensioned to selectively engage and distally advance a drive sled 308 of clip cartridge assembly 300, to thereby effectuate a loading of a surgical clip "C" into the pair of jaws 214, as will be described in greater detail below.

Main drive assembly 220 further includes a shaft pusher tube 223 having a proximal end 223a and a distal end 223b. Proximal end 223a of shaft pusher tube 223 supports an annular flange or cuff 223c thereon. Distal end 223b of shaft pusher tube 223 may include a coupling feature formed therein or define a driving distal-most end 223d.

With reference to FIGS. 2 and 9, endoscopic assembly 200 includes a hollow outer tube 202 having a proximal end 202a and a distal end 202b, and a collar or knob 206 secured to proximal end 202a of outer tube 202. Distal end 202b of outer tube 202 defines a channel or window 202c formed in a side thereof. Outer tube 202 includes a distal shroud 202d extending across window 202c at a distal location of window 202c.

Handle assembly 100, as well as endoscopic assembly 200, may be made from a biocompatible material, such as, for example, a high grade surgical stainless steel, from titanium, or from a high strength autoclavable polymer, thermoplastic or the like.

Endoscopic assembly 200 includes, as seen in FIGS. 2 and 9-12, a pair of jaws 214 mounted in window 202c of outer tube 202 and actuatable by an actuation of trigger 114 of handle assembly 100. The pair of jaws 214 is formed of a suitable biocompatible material such as, for example, stainless steel or titanium. The pair of jaws 214 may be removably or fixedly mounted in channel 202c of outer tube 202.

Referring momentarily to FIGS. 9-12, the pair of jaws 214 defines a channel 214c therebetween for receipt of a surgical clip "C" therein. The pair of jaws 214 include a pair of camming wedge surfaces 214d projecting therefrom. As will be described in detail below, the pair of camming wedge surfaces 214d is acted upon by V-shaped cam groove 222d of distal end 222b of main closure drive rod 222 to actuate the pair of jaws 214 to a closed position.

With continued reference to FIGS. 2 and 9-12, clip cartridge assembly 300 of surgical clip applier 10 is shown. As mentioned above, clip cartridge assembly 300 is configured and dimensioned for selective loading into window 202c formed in distal end 202b of outer tube 202 of endoscopic assembly 200, and is configured and dimensioned to selectively connect, couple or engage distally facing shoulder 222e of main closure drive rod 222, as will be discussed in greater detail below.

Clip cartridge assembly 300 includes a clip tray 302 including base wall, and a pair of spaced apart side walls or rails supported on the base wall, with the base wall and the side walls defining a clip channel therein.

A distal end of the base wall of clip tray 302 may include a resilient central tang (not shown) which is configured and adapted to selectively engage a backspan of a distal-most surgical clip "$C_1$" of the stack of surgical clips "C" retained within clip tray 302 to thereby retain the stack of surgical clips "C" within clip tray 302 of clip cartridge assembly 300.

Clip cartridge assembly 300 includes a cartridge clip pusher bar 304 slidably disposed adjacent clip tray 302. Cartridge clip pusher bar 304 includes a proximal end 304a having a coupling stem 304c projecting therefrom and being connect to or being engagable by a drive sled 308 of clip cartridge assembly 300. Cartridge clip pusher bar 304 further includes a distal end portion 304b defining a pusher 304d configured to engage a distal-most clip "$C_1$" of a stack of clips "C" for loading the distal-most clip "$C_1$" into the pair of jaws 214 of endoscopic assembly 200. Clip pusher bar 304 may further define an elongate window (not shown) therein for operative receipt of a proximal end of a constant force spring 310 therein, as will be discussed in greater detail below.

Clip cartridge assembly 300 includes a stack of surgical clips "C" disposed within the channel of clip tray 302 and adjacent cartridge clip pusher bar 304. Clip cartridge assembly 300 may be loaded with eight (8) surgical clips "C" as shown in the exemplary embodiment illustrated, or, in embodiments, clip cartridge assembly 300 may be loaded with any number of surgical clips "C", provided clip cartridge assembly 300 and endoscopic assembly 200 are each appropriately configured and dimensioned. Surgical clips "C" may be fabricated from materials know by those skilled in the art, including and not limited to stainless steel, titanium, or other metal alloys. In an embodiment it, is contemplated that at least a final surgical clip of the stack of surgical clips "C" may be dyed a particular color to indicate to the user when a final surgical clip of clip cartridge assembly 300 is loaded into the pair of jaws 214.

Clip cartridge assembly 300 further includes a clip follower 306 at least partially slidably disposed within the clip channel of clip tray 302. As will be described in greater detail below, clip follower 306 is positioned proximally of the stack of surgical clips "C" and is provided to help urge the stack of surgical clips "C" forward during an actuation of surgical clip applier 10. Additionally, as will also be described in greater detail below, clip follower 306 is actuated by a constant force spring 310 upon the advancement, by clip pusher bar 304, of the distal-most surgical clip "$C_1$" into the pair of jaws 214, during a firing of surgical clip applier 10.

Clip follower 306 includes an elongate body having a distal end portion configured and dimensioned for passage through the clip channel of clip tray 302. The distal end portion of clip follower 306 is configured to seat against a backspan of a proximal-most clip "$C_p$" of the stack of surgical clips "C".

Clip follower 306 includes a proximal fin 306d projecting transversely from a proximal end portion 306c thereof. Proximal fin 306d of clip follower 306 defines a proximal surface having a concave arcuate profile configured to receive and seat with a coiled or spooled portion 310c of a constant force spring 310.

Clip cartridge assembly 300 includes a drive sled 308 slidably disposed within the clip channel of clip tray 302. Drive sled 308 is configured to selectively engage or be selectively engaged by distally facing shoulder 222e of main closure drive rod 222 of endoscopic assembly 200. Drive sled 308 includes a cartridge pusher rod 308a extending distally therefrom. A distal end of cartridge pusher rod 308a of drive sled 308 is operatively connected to coupling stem 304c of cartridge clip pusher bar 304.

Clip cartridge assembly 300 includes a cartridge cover 312 configured for connection to and supported on clip tray 302. Cartridge cover 312 may include a substantially distally extending hook or tine (not shown) which projects from an inner surface thereof. The hook of cartridge cover 312 is configured to receive and retain a distal end 310b of constant force spring 310. Cartridge cover 312 may be fabricated from a transparent material, allowing the user to clearly see the stack of surgical clips "C".

With particular reference to FIGS. 2 and 10, clip cartridge assembly 300 includes, as mentioned above, a constant force spring 310 supported in the clip channel of clip tray 302. Constant force spring 310 is in the form of a ribbon including a body portion 310a having a distal end 310b, and a proximal end 310c coiled onto itself to form a spool.

Body portion 310a and distal end 310b of constant force spring 310 are disposed within clip channel 302c of clip tray 302 such that body portion 310a and distal end 310b of constant force spring 310 are interposed between cartridge cover 312 and clip pusher bar 304. Distal end 310b of constant force spring 310 is secured to the tine (not shown) of clip cartridge cover 312, as mentioned above. It is contemplated that distal end 310b of constant force spring 310 may define an opening therein that is slipped over the distally extending tine of clip cartridge cover 312. In this manner, the tine of clip cartridge cover 312 prevents distal end 310b of constant force spring 310 from moving proximally.

Proximal coiled or spooled end 310c of constant force spring 310 is disposed proximally of proximal fin 306d of clip follower 306. Due to a memory of constant force spring 310, proximal coiled or spooled end 310c thereof tends to want to roll-up onto itself along body portion 310a.

Constant force spring 310 is a pre-stressed flat strip of spring material which is formed into a virtually constant radius coil, wherein distal end 310b of constant force spring 310 is secured to the tine of clip cartridge cover 312, as described above, and wherein proximal coiled or spooled end 310c of constant force spring 310 is disposed proximally of proximal fin 306d of clip follower 306, as described above.

Constant force spring 310 functions to maintain a constant pressure or distal force on clip follower 306, and in turn on the stack of surgical clips "C" such that the stack of surgical clips "C" are pressed against the resilient central tang (not shown) of clip tray 302. In this manner, in operation, as will be described in greater detail below, the stack of surgical clips "C" advances distally, on demand, as clip pusher bar 304 distally advances the distal-most surgical clip "$C_1$" any amount, and in particular, past the resilient central tang of clip tray 302.

With continued reference to FIGS. 1-18C, an exemplary mode of operation of clip applier 10 is shown and described. As shown in FIGS. 1 and 14-17, clip applier 10 is illustrated with clip cartridge assembly 300 connected to distal end of endoscopic assembly 200 such that drive sled 308 of clip cartridge assembly 300 is in operative engagement with distally facing shoulder 222e of main closure drive rod 222 of endoscopic assembly 200 (as described above).

With reference to FIGS. 14, 15, 18A and 18B, when trigger 114 is squeezed or pivoted about pivot shaft 116, actuating end 114b of trigger 114 engages the proximal end of main closure drive rod 222 of endoscopic assembly 200 thereby urging main closure drive rod 222 distally.

As main closure drive rod 222 of endoscopic assembly 200 is distally advanced, due to an actuation of trigger 114, enlarged proximal end 222a of main closure drive rod 222 acts on a biasing member 225 (e.g., a compression spring) which in turn acts on cuff 223c of shaft pusher tube 223 to distally advance shaft pusher tube 223. As shaft pusher tube 223 is advanced distally, a distal end 223d of shaft pusher tube 223 acts on coupling stem 304c of cartridge clip pusher bar 304 to distally advance cartridge clip pusher bar 304. Shaft pusher tube 223 is advanced distally until cuff 223c of shaft pusher tube 223 abuts a stopper 227 (see FIGS. 2, 15 and 17) of endoscopic assembly 200. At this point, shaft pusher tube 223 comes to a stop and rests.

When trigger 114 of handle assembly 100 is squeezed this initial amount, clip pusher bar 304 will have advanced an amount sufficient to distally advance a distal-most surgical clip "$C_1$" past the resilient central tang of clip tray 302 and load the distal-most surgical clip "$C_1$" into the pair of jaws 214. Specifically, pusher 304d of cartridge clip pusher bar 304 is moved in a distal direction such that pusher 304d engages the backspan of distal-most clip "$C_1$" and pushes distal-most clip "$C_1$" distally, out of clip tray 302 and into the pair of jaws 214.

As clip pusher bar 304 is advanced distally, and distal-most surgical clip "$C_1$" is being advanced and loaded into the pair of jaws 214, constant force spring 310 is actuated such that spooled end 310c of constant force spring 310 presses on proximal fin 306d of clip follower 306 to distally advance the stack of surgical clips "C" until the next distal-most clip engages and is stopped by the resilient central tang of clip tray 302.

Clip pusher bar 304 will remain in a distally advanced position during the entire squeeze of trigger 114. Following a squeeze of trigger 114, as trigger 114 is released or returned to a full non-squeezed position, clip pusher bar 304 is returned to a home or proximal-most position by a biasing member or the like (not shown). When clip pusher bar 304 is returned to the home position, pusher 304d of clip pusher bar 304 is moved to a position proximal of the new distal-most surgical clip "$C_1$".

Figure 18A:
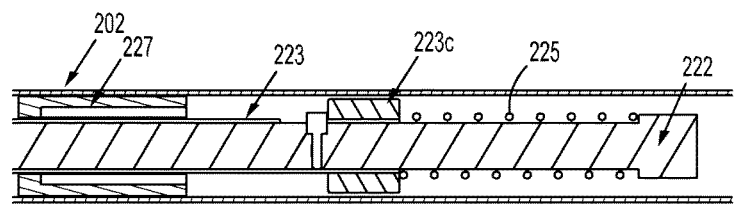
FIGS. 18A-18C are enlarged views illustrating an operation of a drive mechanism of the endoscopic shaft assembly of FIGS. 1-17.
Figure 18B:
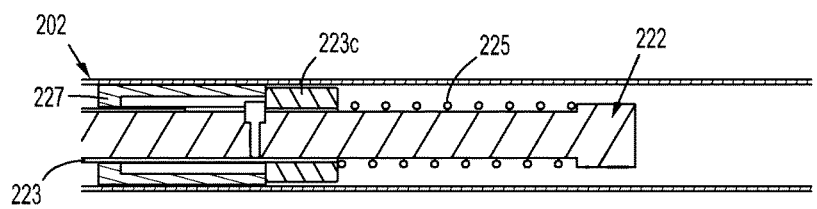
Figure 18C:
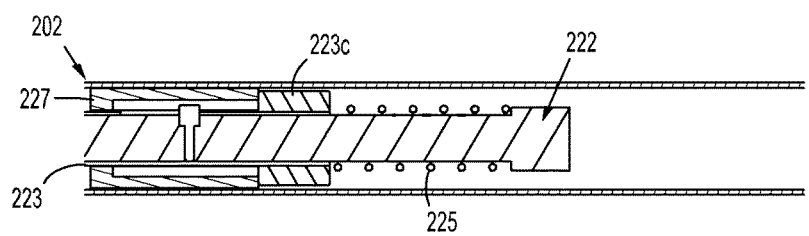

Additionally, with reference to FIGS. 18B and 18C, as main closure drive rod 222 of endoscopic assembly 200 is distally advanced, due to a further actuation of trigger 114 beyond the initial amount, after cuff 223c of shaft pusher tube 223 abuts stopper 227, actuating end 114b of trigger 114 continues to distally advance main closure drive rod 222 and compress biasing member 225 between enlarged proximal end 222a of main closure drive rod 222 and cuff 223c of shaft pusher tube 223. As main closure drive rod 222 is continued to be advanced distally, following a dwell period, V-shaped cam groove 222d of main closure drive rod 222 is advanced distally into engagement with cam wedges 214d of the pair of jaws 214 of endoscopic assembly 200, to thereby effectuate a closure or approximation of the pair of jaws 214 and a formation of the distal-most clip "C1" loaded therewith.

Following formation of the distal-most clip "C1", trigger 114 may be released, whereby main closure drive rod 222 is moved in a proximal direction until main drive rod 122 is returned to a proximal-most position thereof. When main drive rod 122 is returned to the proximal-most position thereof, V-shaped cam groove 222d of main closure drive rod 222 is proximally withdrawn from cam wedges 214d of the pair of jaws 214 of endoscopic assembly 200 to permit the pair of jaws 214 to open as a result of their own resilient bias.

Also, when main drive rod 122 is returned to the proximal-most position thereof, biasing member 225 is permitted to expand and shaft pusher tube 223 is permitted to return to a proximal-most position thereof. As shaft pusher tube 223 returns to the proximal-most position thereof, clip pusher bar 304 is also returned to a proximal-most position thereof, as described above.

The operations described above can be repeated, as required, until all of the surgical clips "C" have been fired and formed.

Turning now to FIGS. 19-22C, an endoscopic assembly according to an alternate embodiment of the disclosure is generally designated as 400. Endoscopic assembly 400 includes a hollow outer tube 402 having a proximal end 402a and a distal end 402b defining a channel or window 402c formed in a side thereof. Hollow outer tube 402 includes a shoulder 402d extending radially into window 402c.

Main drive assembly 420 includes a main closure drive rod 422 having a proximal end 422a and a distal end 422b. Main closure drive rod 422 defines a channel 422c therein. Channel 422c of main closure drive rod 422 includes a proximal bore or recess 422d having a distal surface or shoulder 422e near a proximal end thereof, and a proximal face 422f.

Main drive assembly 420 further includes a shaft pusher rod 423 slidably disposed within channel 422c of main closure drive rod 422. Shaft pusher rod 423 includes a proximal end or stem 423a and a distal end or stem 423b, wherein a shoulder defining a proximally facing surface 423c is defined between proximal stem 423a and distal stem 423b. Proximal stem 423a of shaft pusher rod 423 extends into proximal bore 422d of channel 422c of main closure drive rod 422. Distal stem 423b of shaft pusher rod 423 extends distally of shoulder 402d of hollow outer tube 402.

Main drive assembly 420 also includes a biasing member 425 (e.g., a compression spring) supported on proximal stem 423a of shaft pusher rod 423 and interposed between distal surface or shoulder 422e of main closure drive rod 422 and proximally facing surface 423c of shaft pusher rod 423.

With continued reference to FIGS. 19-22C, an exemplary mode of operation of clip applier 10, including endoscopic assembly 400, is shown and described. In operation, when trigger 114 is squeezed or pivoted about pivot shaft 116, actuating end 114b of trigger 114 engages the proximal end of main closure drive rod 422 of endoscopic assembly 400 thereby urging main closure drive rod 422 distally.

As main closure drive rod 422 of endoscopic assembly 400 is distally advanced, due to an actuation of trigger 114, shoulder 422e of main closure drive rod 422 acts on biasing member 425, which in turn acts on proximally facing surface 423c of shaft pusher rod 423 to distally advance shaft pusher rod 423. As shaft pusher rod 423 is advanced distally, a distal end of distal stem 423b of shaft pusher rod 423 acts on a coupling stem or feature (e.g., coupling stem 304c) of cartridge clip pusher bar 304 to distally advance cartridge clip pusher bar 304. Shaft pusher rod 423 is advanced distally until shoulder 423c thereof abuts shoulder 402d of hollow outer tube 402, and comes to a stop and rests.

When trigger 114 of handle assembly 100 is squeezed this initial amount clip pusher bar 304 will have advanced an amount sufficient to distally advance a distal-most surgical clip "$C_1$" past the resilient central tang of clip tray 302 and load the distal-most surgical clip "$C_1$" into the pair of jaws 214. Specifically, pusher 304d of cartridge clip pusher bar 304 is moved in a distal direction such that pusher 304d engages the backspan of distal-most clip "$C_1$" and pushes distal-most clip "$C_1$" distally, out of clip tray 302 and into the pair of jaws 214.

As clip pusher bar 304 is advanced distally, and distal-most surgical clip "$C_1$" is being advanced and loaded into the pair of jaws 214, constant force spring 310 is actuated such that spooled end 310c of constant force spring 310 presses on proximal fin 306d of clip follower 306 to distally advance the stack of surgical clips "C" until the next distal-most clip engages and is stopped by the resilient central tang of clip tray 302.

Clip pusher bar 304 will remain in a distally advanced position during the entire squeeze of trigger 114. Following a full squeeze of trigger 114, as trigger 114 is released or returned to a full non-squeezed position, clip pusher bar 304 is returned to a home or proximal-most position by a biasing member or the like (not shown). When clip pusher bar 304 is returned to the home position, pusher 304d of clip pusher bar 304 is moved to a position proximal of the new distal-most surgical clip "$C_1$".

Figure 22A:
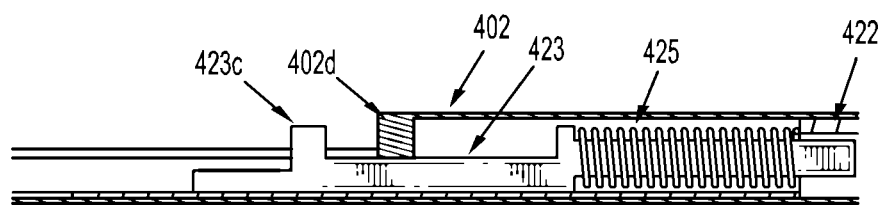
FIGS. 22A-22C are enlarged views illustrating an operation of a drive mechanism of the endoscopic shaft assembly of FIGS. 19-21.
Figure 22B:
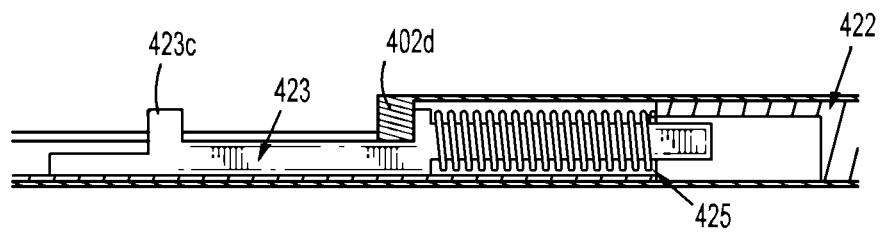
Figure 22C:
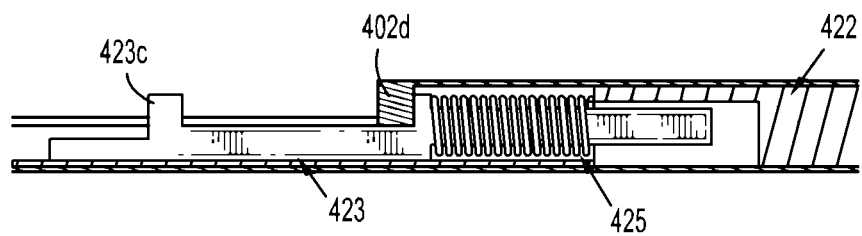

Additionally, with reference to FIGS. 22B and 22C, as main closure drive rod 422 of endoscopic assembly 400 is distally advanced, due to a further actuation of trigger 114 beyond the initial squeeze, after shoulder 423c of shaft pusher rod 423 abuts shoulder 402d of hollow outer tube 402, actuating end 114b of trigger 114 continues to distally advance main closure drive rod 422 and compress biasing member 425 between shoulder 423c of shaft pusher rod 423 and shoulder 422e of main closure drive rod 422. As main closure drive rod 422 is continued to be advanced distally, following a dwell period, a distal end of main closure drive rod 422 is advanced distally effectuate an engagement with cam wedges 214d of the pair of jaws 214 of endoscopic assembly 400, to thereby effectuate a closure or approximation of the pair of jaws 214 and a formation of the distal-most clip "$C_1$" loaded therewith.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A reposable surgical clip applier, comprising:
   a handle assembly including:
      a housing defining a bore therein;
      a fixed handle extending from the housing; and
      a trigger pivotally connected to the fixed handle, the trigger including an actuating end disposed within the bore of the housing;
   an endoscopic assembly selectively connectable to the housing of the handle assembly, the endoscopic assembly including:
      an outer tube defining a lumen therethrough, the outer tube including a proximal end and a distal end;
      a pair of jaws fixedly supported and extending from the distal end of the outer tube; and
      a drive assembly slidably supported in the lumen of the outer tube, the drive assembly including:

a shaft pusher tube slidably supported in the lumen of the outer tube, the shaft pusher tube including a proximal end, a distal end and defining a lumen therethrough, wherein a radial flange is provided at the proximal end of the shaft pusher tube;

a closure drive rod slidably disposed within the lumen of the shaft pusher tube, the closure drive rod having a proximal end projecting from the proximal end of the outer tube and engagable by the actuating end of the trigger, and a distal end selectively engagable with the pair of jaws to approximate the pair of jaws, wherein a shoulder is provided at the proximal end of the closure drive rod; and a biasing member interposed between the shoulder of the closure drive rod and the radial flange of the shaft pusher tube, wherein the biasing member of the drive assembly translates together with the closure drive rod during an initial actuation of the trigger; and a clip cartridge assembly selectively connectable to the distal end of the outer tube, and to the distal end of the shaft pusher tube, the clip cartridge assembly including:

a clip tray;

a plurality of surgical clips slidably supported in the clip tray;

a clip follower slidably disposed within the clip tray and disposed proximal of the plurality of surgical clips;

a biasing member tending to urge the clip follower in a distal direction; and a clip pusher bar slidably supported adjacent the clip tray, wherein the clip pusher bar includes a proximal end configured for engagement by the distal end of the shaft pusher tube, and a distal end configured to engage a distal-most clip of the plurality of surgical clips.

2. The reposable surgical clip applier according to claim 1, wherein during the initial actuation of the trigger, the actuating end of the trigger acts on the proximal end of the closure drive rod of the endoscopic assembly to distally advance the closure drive rod, wherein the closure drive rod acts on the biasing member to distally advance the biasing member against the radial flange of the shaft pusher tube to distally advance the shaft pusher tube, and wherein the shaft pusher tube acts on the clip pusher bar to distally advance the clip pusher bar of the clip cartridge assembly and load a distal-most surgical clip thereof into the pair of jaws.

3. The reposable surgical clip applier according to claim 2, wherein the endoscopic assembly includes a stop member supported in the outer tube thereof, wherein the stop member is disposed distal of the radial flange of the shaft pusher tube.

4. The reposable surgical clip applier according to claim 3, wherein the distal advancement of the shaft pusher tube is stopped by the stop member.

5. The reposable surgical clip applier according to claim 4, wherein following the stop member stopping the distal advancement of the shaft pusher tube, during a further actuation of the trigger, the actuating end of the trigger acts on the proximal end of the closure drive rod of the endoscopic assembly to further distally advance the closure drive rod, wherein the closure drive rod acts on the biasing member of the drive assembly to compress the biasing member between the radial flange of the shaft pusher tube and the shoulder of the closure drive rod.

6. The reposable surgical clip applier according to claim 5, wherein during the further actuation of the trigger, the distal end of the closure drive rod acts on the pair of jaws to approximate the pair of jaws and to form any surgical clip loaded therein.

7. The reposable surgical clip applier according to claim 6, wherein the clip pusher bar of the clip cartridge assembly remains in a distal position during the approximation of the pair of jaws.

8. The reposable surgical clip applier according to claim 1, wherein the handle assembly includes an end cap selectively securable to a proximal end of the housing.

9. An endoscopic assembly configured for selective connection to a handle assembly and actuatable by a trigger of the handle assembly, the endoscopic assembly comprising:

an outer tube defining a lumen therethrough, the outer tube including a proximal end and a distal end;

a pair of jaws fixedly supported and extending from the distal end of the outer tube, the pair of jaws being movable between an open position and a closed position, wherein the pair of jaws are configured to form a surgical clip loaded therewithin when the pair of jaws are actuated from the open position to the closed position; and a drive assembly slidably supported in the lumen of the outer tube, the drive assembly including:

a shaft pusher tube slidably supported in the lumen of the outer tube, the shaft pusher tube including a proximal end, a distal end and defining a lumen therethrough, wherein a radial flange is provided at the proximal end of the shaft pusher tube; and a closure drive rod slidably disposed within the lumen of the shaft pusher tube, the closure drive rod having a proximal end projecting from the proximal end of the outer tube and engagable by the trigger of the handle assembly, and a distal end configured to selectively engage the pair of jaws to move the pair of jaws to the closed position, wherein a shoulder is provided at the proximal end of the closure drive rod; and a biasing member interposed between the shoulder of the closure drive rod and the radial flange of the shaft pusher tube, wherein the biasing member of the drive assembly translates together with the closure drive rod during an initial actuation of the trigger.

10. The endoscopic assembly according to claim 9, wherein during an initial distal advancement of closure drive rod, the shoulder of the closure drive rod acts on the biasing member to distally advance the biasing member against the radial flange of the shaft pusher tube to distally advance the shaft pusher tube, and wherein the shaft pusher tube acts on a clip cartridge assembly loaded in the outer tube to advance a distal-most surgical clip of the clip cartridge assembly into the pair of jaws.

11. The endoscopic assembly according to claim 10, wherein the endoscopic assembly includes a stop member supported in the outer tube thereof, wherein the stop member is disposed distal of the radial flange of the shaft pusher tube.

12. The endoscopic assembly according to claim 11, wherein the distal advancement of the shaft pusher tube is stopped by the stop member.

13. The endoscopic assembly according to claim 12, wherein following the stop member stopping the distal advancement of the shaft pusher tube, during a further advancement of the closure drive rod, the closure drive rod acts on the biasing member to compress the biasing member between the radial flange of the shaft pusher tube and the shoulder of the closure drive rod.

14. The endoscopic assembly according to claim 13, wherein during the further advancement of the closure drive rod, the distal end of the closure drive rod acts on the pair of jaws to approximate the pair of jaws and to form any surgical clip loaded therein.

15. A reposable surgical clip applier, comprising:
a handle assembly including:
   a housing; and
   a trigger pivotally connected to the housing, the trigger including an actuating end disposed within the housing;
an endoscopic assembly selectively connectable to the housing of the handle assembly, the endoscopic assembly including:
   an outer tube defining a lumen therethrough and a window in a distal end thereof;
   a pair of jaws fixedly supported and extending from the distal end of the outer tube; and
   a drive assembly slidably supported in the lumen of the outer tube, the drive assembly including:
      a shaft pusher tube slidably supported in the lumen of the outer tube, the shaft pusher tube including a proximal end, a distal end and defining a lumen therethrough, wherein a radial flange is provided at the proximal end of the shaft pusher tube;
      a closure drive rod slidably disposed within the lumen of the shaft pusher tube, the closure drive rod having a proximal end projecting from the proximal end of the outer tube and engagable by the actuating end of the trigger, and a distal end selectively engagable with the pair of jaws to approximate the pair of jaws, wherein a shoulder is provided at the proximal end of the closure drive rod; and
      a biasing member interposed between the shoulder of the closure drive rod and the radial flange of the shaft pusher tube, wherein the biasing member of the drive assembly translates together with the closure drive rod during an initial actuation of the trigger; and
a clip cartridge assembly selectively disposable within the window of the outer tube, and selectively connectable to the distal end of the shaft pusher tube, the clip cartridge assembly including:
   a clip tray;
   a plurality of surgical clips slidably supported in the clip tray;
   a clip follower slidably disposed within the clip tray and disposed proximal of the plurality of surgical clips;
   a biasing member tending to urge the clip follower in a distal direction; and
   a clip pusher bar slidably supported adjacent the clip tray, wherein the clip pusher bar includes a proximal end configured for engagement by the distal end of the shaft pusher tube, and a distal end configured to engage a distal-most clip of the plurality of surgical clips.

16. The reposable surgical clip applier according to claim 15, wherein during the initial actuation of the trigger, the actuating end of the trigger acts on the proximal end of the closure drive rod of the endoscopic assembly to distally advance the closure drive rod, wherein the closure drive rod acts on the biasing member to distally advance the biasing member against the radial flange of the shaft pusher tube to distally advance the shaft pusher tube, and wherein the shaft pusher tube acts on the clip pusher bar to distally advance the clip pusher bar of the clip cartridge assembly and load a distal-most surgical clip thereof into the pair of jaws.

17. The reposable surgical clip applier according to claim 16, wherein the endoscopic assembly includes a stop member supported in the outer tube thereof, wherein the stop member is disposed distal of the radial flange of the shaft pusher tube.

18. The reposable surgical clip applier according to claim 17, wherein the distal advancement of the shaft pusher tube is stopped by the stop member.

19. The reposable surgical clip applier according to claim 18, wherein following the stop member stopping the distal advancement of the shaft pusher tube, during a further actuation of the trigger, the actuating end of the trigger acts on the proximal end of the closure drive rod of the endoscopic assembly to further distally advance the closure drive rod, wherein the closure drive rod acts on the biasing member of the drive assembly to compress the biasing member between the radial flange of the shaft pusher tube and the shoulder of the closure drive rod.

20. The reposable surgical clip applier according to claim 19, wherein during the further actuation of the trigger, the distal end of the closure drive rod acts on the pair of jaws to approximate the pair of jaws and to form any surgical clip loaded therein.

21. The reposable surgical clip applier according to claim 20, wherein the clip pusher bar of the clip cartridge assembly remains in a distal position during the approximation of the pair of jaws.

* * * * *